(12) United States Patent
Markle et al.

(10) Patent No.: US 8,467,843 B2
(45) Date of Patent: Jun. 18, 2013

(54) OPTICAL SENSOR CONFIGURATION FOR RATIOMETRIC CORRECTION OF BLOOD GLUCOSE MEASUREMENT

(75) Inventors: David R. Markle, Berwyn, PA (US); Soya Gamsey, Huntington Beach, CA (US); Thomas A. Peyser, Menlo Park, CA (US)

(73) Assignee: Glumetrics, Inc., Irvine, CA (US)

( * ) Notice: Subject to any disclaimer, the term of this patent is extended or adjusted under 35 U.S.C. 154(b) by 661 days.

(21) Appl. No.: 12/612,602

(22) Filed: Nov. 4, 2009

(65) Prior Publication Data
US 2011/0105866 A1 May 5, 2011

(51) Int. Cl.
*A61B 5/00* (2006.01)
(52) U.S. Cl.
USPC ........... 600/316; 600/309; 600/364; 600/365; 600/366
(58) Field of Classification Search
USPC ................ 600/316, 309, 317, 337, 365, 364, 600/366
See application file for complete search history.

(56) References Cited

U.S. PATENT DOCUMENTS

| | | |
|---|---|---|
| 1,120,700 A | 12/1914 | Ehrlich |
| 1,334,901 A | 3/1920 | Higdon |
| 2,112,244 A | 3/1938 | Jurist |
| 2,274,551 A | 2/1942 | Kenyon et al. |
| 2,496,151 A | 1/1950 | Dawson et al. |
| 2,812,524 A | 11/1957 | Pruitt |
| 3,011,293 A | 12/1961 | Rado |
| 3,302,219 A | 2/1967 | Harris |
| 3,488,098 A | 1/1970 | Sobczak |
| 3,659,586 A | 5/1972 | Johns et al. |
| 3,795,239 A | 3/1974 | Eberhard et al. |
| 3,827,089 A | 8/1974 | Grow |
| 3,865,548 A | 2/1975 | Padawer |
| 3,874,010 A | 4/1975 | Geary |
| 3,884,225 A | 5/1975 | Witter |
| 3,895,403 A | 7/1975 | Davis |
| 3,905,888 A | 9/1975 | Mindt et al. |
| 3,909,504 A | 9/1975 | Browne |
| 3,924,281 A | 12/1975 | Gibbs |
| 3,930,580 A | 1/1976 | Bazell et al. |

(Continued)

FOREIGN PATENT DOCUMENTS

| | | |
|---|---|---|
| CN | 85108331 | 6/1987 |
| CS | 7707425 | 2/1980 |

(Continued)

OTHER PUBLICATIONS

PCT International Search Report re PCT/US2010/044761 dated Oct. 6, 2010.

(Continued)

*Primary Examiner* — Rochelle-Ann J Blackman
(74) *Attorney, Agent, or Firm* — Knobbe Martens Olson & Bear, LLP

(57) ABSTRACT

Embodiments of the invention are directed to an optical sensor for detecting blood glucose. The sensor comprises a chemical indicator system disposed within a gap between the distal end of an optical fiber and an atraumatic tip portion, wherein the optical fiber and atraumatic tip portion are coupled by a coupling member, such as a rod or hypotube or cage that traverses the gap. The sensor further comprises a means for generating and detecting an optical reference signal unrelated to the blood glucose, such that ratiometric correction of blood glucose measurements for artifacts in the optical system is enabled.

27 Claims, 20 Drawing Sheets

U.S. PATENT DOCUMENTS

| | | | |
|---|---|---|---|
| 3,996,345 A | 12/1976 | Ullman | |
| 4,003,707 A | 1/1977 | Lübbers et al. | |
| 4,041,932 A | 8/1977 | Fostick | |
| 4,094,578 A | 6/1978 | DiVita et al. | |
| 4,180,879 A | 1/1980 | Mann | |
| 4,197,853 A | 4/1980 | Parker | |
| 4,200,110 A | 4/1980 | Peterson et al. | |
| 4,245,645 A | 1/1981 | Arseneault et al. | |
| 4,269,605 A | 5/1981 | Dean et al. | |
| 4,306,562 A | 12/1981 | Osborne | |
| 4,307,933 A | 12/1981 | Palmer et al. | |
| 4,308,254 A | 12/1981 | Tayot et al. | |
| 4,344,438 A | 8/1982 | Schultz | |
| 4,345,606 A | 8/1982 | Littleford | |
| 4,358,851 A | 11/1982 | Scilfres et al. | |
| 4,361,918 A | 12/1982 | Roisseth | |
| 4,371,374 A | 2/1983 | Cerami et al. | |
| 4,459,712 A | 7/1984 | Pathan | |
| 4,465,335 A | 8/1984 | Eppes | |
| 4,469,357 A | 9/1984 | Martin | |
| 4,474,431 A | 10/1984 | Bricheno | |
| 4,476,870 A | 10/1984 | Peterson et al. | |
| 4,490,867 A | 1/1985 | Gabrielsson | |
| 4,495,293 A | 1/1985 | Shaffar | |
| 4,502,169 A | 3/1985 | Persson | |
| RE31,879 E | 5/1985 | Lübbers et al. | |
| 4,528,616 A | 7/1985 | Koppensteiner | |
| 4,548,907 A | 10/1985 | Seitz et al. | |
| 4,557,900 A | 12/1985 | Heitzmann | |
| 4,560,248 A | 12/1985 | Cramp et al. | |
| 4,568,444 A | 2/1986 | Nakamura et al. | |
| 4,600,310 A | 7/1986 | Cramp et al. | |
| 4,621,049 A | 11/1986 | Wang | |
| 4,629,451 A | 12/1986 | Winters et al. | |
| 4,636,144 A | 1/1987 | Abe et al. | |
| 4,649,271 A | 3/1987 | Hök et al. | |
| 4,650,472 A | 3/1987 | Bates | |
| 4,654,031 A | 3/1987 | Lentz | |
| 4,659,817 A | 4/1987 | Gallop et al. | |
| 4,675,925 A | 6/1987 | Littleton | |
| 4,684,538 A | 8/1987 | Klemarczyk | |
| RE32,514 E | 10/1987 | Steklenski | |
| 4,703,756 A | 11/1987 | Gough et al. | |
| 4,707,056 A | 11/1987 | Bittner | |
| 4,710,623 A | 12/1987 | Lipson et al. | |
| 4,727,730 A | 3/1988 | Boiarski et al. | |
| 4,737,153 A | 4/1988 | Shimamura et al. | |
| 4,744,618 A | 5/1988 | Mahlein | |
| 4,746,751 A | 5/1988 | Oviatt | |
| 4,750,795 A | 6/1988 | Blotekjaer | |
| 4,751,918 A | 6/1988 | Bernard et al. | |
| 4,754,538 A | 7/1988 | Stewart, Jr. et al. | |
| 4,776,047 A | 10/1988 | DiMatteo | |
| 4,785,814 A | 11/1988 | Kane | |
| 4,794,619 A | 12/1988 | Tregay | |
| 4,796,633 A | 1/1989 | Zwirkoski | |
| 4,798,738 A | 1/1989 | Yafuso et al. | |
| 4,801,187 A | 1/1989 | Elbert et al. | |
| 4,803,049 A | 2/1989 | Hirschfeld et al. | |
| 4,816,130 A | 3/1989 | Karakelle et al. | |
| 4,820,636 A | 4/1989 | Hill et al. | |
| 4,821,738 A | 4/1989 | Iwasaki et al. | |
| 4,822,127 A | 4/1989 | Kamiya et al. | |
| 4,833,091 A | 5/1989 | Leader et al. | |
| 4,838,269 A | 6/1989 | Robinson et al. | |
| 4,846,543 A | 7/1989 | Kapany et al. | |
| 4,851,195 A | 7/1989 | Matthews et al. | |
| 4,854,321 A | 8/1989 | Boiarski | |
| 4,861,728 A | 8/1989 | Wagner | |
| 4,872,226 A | 10/1989 | Lonardo | |
| 4,872,759 A | 10/1989 | Stich-Baumeister | |
| 4,886,338 A | 12/1989 | Yafuso et al. | |
| 4,889,407 A | 12/1989 | Markle et al. | |
| 4,903,707 A | 2/1990 | Knute et al. | |
| 4,906,232 A | 3/1990 | Reynolds | |
| 4,923,273 A | 5/1990 | Taylor | |
| 4,927,222 A | 5/1990 | Kamiya et al. | |
| 4,937,901 A | 7/1990 | Brennan | |
| 4,939,801 A | 7/1990 | Schaal et al. | |
| 4,941,308 A | 7/1990 | Grabenkort et al. | |
| 4,943,364 A | 7/1990 | Koch et al. | |
| 4,946,038 A | 8/1990 | Eaton | |
| 4,955,862 A | 9/1990 | Sepetka | |
| 4,960,412 A | 10/1990 | Fink | |
| 4,966,597 A | 10/1990 | Cosman | |
| 5,000,901 A | 3/1991 | Iyer et al. | |
| 5,005,576 A | 4/1991 | Günther | |
| 5,007,704 A | 4/1991 | McCartney | |
| 5,012,809 A | 5/1991 | Shulze | |
| 5,018,225 A | 5/1991 | Fergni et al. | |
| 5,030,420 A | 7/1991 | Bacon | |
| 5,047,208 A | 9/1991 | Schweitzer et al. | |
| 5,047,627 A | 9/1991 | Yim et al. | |
| 5,054,497 A | 10/1991 | Kapp et al. | |
| 5,068,931 A | 12/1991 | Smith | |
| 5,069,674 A | 12/1991 | Fearnot et al. | |
| 5,082,112 A | 1/1992 | Dunklee | |
| 5,093,266 A | 3/1992 | Leader et al. | |
| 5,098,618 A | 3/1992 | Zelez | |
| 5,104,388 A | 4/1992 | Quackenbush | |
| 5,108,502 A | 4/1992 | Pawlowski et al. | |
| 5,109,452 A | 4/1992 | Selvin et al. | |
| 5,114,676 A | 5/1992 | Leiner et al. | |
| 5,119,463 A | 6/1992 | Vurek | |
| 5,137,833 A | 8/1992 | Russell | |
| 5,141,497 A | 8/1992 | Erskine | |
| 5,162,130 A | 11/1992 | McLaughlin | |
| 5,166,990 A | 11/1992 | Riccitelli et al. | |
| 5,167,715 A | 12/1992 | Kalafala et al. | |
| 5,168,587 A | 12/1992 | Shutes | |
| 5,175,016 A | 12/1992 | Yafuso et al. | |
| 5,176,882 A | 1/1993 | Gray et al. | |
| 5,178,267 A | 1/1993 | Grabenkort et al. | |
| 5,180,376 A | 1/1993 | Fischell | |
| 5,182,353 A | 1/1993 | Hui et al. | |
| 5,185,263 A | 2/1993 | Kroneis et al. | |
| 5,217,691 A | 6/1993 | Greene et al. | |
| 5,230,031 A | 7/1993 | Markle | |
| 5,246,109 A | 9/1993 | Markle et al. | |
| 5,246,441 A | 9/1993 | Ross et al. | |
| 5,257,338 A | 10/1993 | Markle | |
| 5,262,037 A | 11/1993 | Markle et al. | |
| 5,279,596 A | 1/1994 | Castaneda et al. | |
| 5,280,130 A | 1/1994 | Markle et al. | |
| 5,280,548 A | 1/1994 | Atwater et al. | |
| 5,286,294 A | 2/1994 | Ebi et al. | |
| 5,290,266 A | 3/1994 | Rohling et al. | |
| 5,302,731 A | 4/1994 | Pitner et al. | |
| 5,305,740 A | 4/1994 | Kolobow | |
| 5,310,471 A | 5/1994 | Markle et al. | |
| 5,312,344 A | 5/1994 | Grinfeld | |
| 5,322,513 A | 6/1994 | Walker | |
| 5,334,157 A | 8/1994 | Klein et al. | |
| 5,354,448 A | 10/1994 | Markle et al. | |
| 5,357,732 A | 10/1994 | Markle et al. | |
| 5,361,758 A | 11/1994 | Hall et al. | |
| 5,380,304 A | 1/1995 | Parker | |
| 5,389,217 A | 2/1995 | Singer | |
| 5,409,469 A | 4/1995 | Schaerf | |
| 5,503,770 A | 4/1996 | James et al. | |
| 5,511,408 A | 4/1996 | Yoshioka et al. | |
| 5,511,547 A | 4/1996 | Markle et al. | |
| 5,512,246 A | 4/1996 | Russell et al. | |
| 5,545,179 A | 8/1996 | Williamson, IV | |
| 5,558,714 A | 9/1996 | Watanabe et al. | |
| 5,569,186 A | 10/1996 | Lord et al. | |
| 5,596,988 A | 1/1997 | Markle et al. | |
| 5,618,587 A | 4/1997 | Markle et al. | |
| 5,622,259 A | 4/1997 | Church | |
| 5,634,911 A | 6/1997 | Hermann et al. | |
| 5,643,212 A | 7/1997 | Coutre et al. | |
| 5,658,264 A | 8/1997 | Samson | |
| 5,669,920 A | 9/1997 | Conley et al. | |
| 5,676,784 A | 10/1997 | McGaffigan | |
| D388,418 S | 12/1997 | Polson et al. | |
| 5,700,253 A | 12/1997 | Parker | |
| 5,702,373 A | 12/1997 | Samson | |

| Patent No. | Date | Name |
|---|---|---|
| 5,747,666 A | 5/1998 | Willis |
| 5,755,704 A | 5/1998 | Lunn |
| 5,763,238 A | 6/1998 | James et al. |
| 5,797,876 A | 8/1998 | Spears et al. |
| 5,810,985 A | 9/1998 | Bao et al. |
| 5,827,242 A | 10/1998 | Follmer et al. |
| 5,891,100 A | 4/1999 | Fleckenstein |
| 5,891,114 A | 4/1999 | Chien et al. |
| 5,922,612 A | 7/1999 | Alder et al. |
| 5,947,940 A | 9/1999 | Beisel |
| 5,951,929 A | 9/1999 | Wilson |
| 5,954,651 A | 9/1999 | Berg et al. |
| 6,002,954 A | 12/1999 | Van Antwerp et al. |
| 6,011,984 A | 1/2000 | Van Antwerp et al. |
| 6,019,736 A | 2/2000 | Avellanet et al. |
| 6,152,933 A | 11/2000 | Werp et al. |
| 6,156,010 A | 12/2000 | Kuracina et al. |
| 6,187,130 B1 | 2/2001 | Berard et al. |
| 6,200,301 B1 | 3/2001 | Pfeiffer et al. |
| 6,273,874 B1 | 8/2001 | Parris |
| 6,304,766 B1 | 10/2001 | Colvin, Jr. |
| 6,319,540 B1 | 11/2001 | Van Antwerp et al. |
| 6,363,273 B1 | 3/2002 | Mastrorio et al. |
| 6,370,406 B1 | 4/2002 | Wach et al. |
| 6,375,627 B1 | 4/2002 | Mauze |
| 6,464,849 B1 | 10/2002 | Say et al. |
| 6,544,212 B2 | 4/2003 | Galley et al. |
| 6,584,335 B1 | 6/2003 | Haar et al. |
| 6,585,665 B1 | 7/2003 | Chapman et al. |
| 6,602,702 B1 | 8/2003 | McDevitt et al. |
| 6,623,490 B1 | 9/2003 | Crane et al. |
| 6,627,177 B2 | 9/2003 | Singaram et al. |
| 6,653,141 B2 | 11/2003 | Singaram et al. |
| 6,663,595 B2 | 12/2003 | Spohn et al. |
| 6,702,972 B1 | 3/2004 | Markle |
| 6,711,423 B2 | 3/2004 | Colvin |
| 6,766,183 B2 | 7/2004 | Walsh et al. |
| 6,794,195 B2 | 9/2004 | Colvin, Jr. |
| 6,800,451 B2 | 10/2004 | Daniloff et al. |
| 6,804,544 B2 | 10/2004 | Van Antwerp et al. |
| D525,632 S | 7/2006 | Jost et al. |
| 7,181,260 B2 | 2/2007 | Gutierrez |
| D544,871 S | 6/2007 | Lim et al. |
| 7,226,414 B2 | 6/2007 | Ballerstadt |
| 7,229,450 B1 | 6/2007 | Chitre et al. |
| D550,242 S | 9/2007 | Niijima |
| D550,245 S | 9/2007 | Niijima |
| 7,277,740 B2 | 10/2007 | Rohleder et al. |
| D559,264 S | 1/2008 | Niijima |
| D560,224 S | 1/2008 | Park et al. |
| 7,353,055 B2 | 4/2008 | Hogan |
| 7,358,094 B2 | 4/2008 | Bell et al. |
| 7,381,938 B2 | 6/2008 | Kobayashi et al. |
| 7,390,462 B2 | 6/2008 | Rao et al. |
| 7,417,164 B2 | 8/2008 | Suri |
| D580,950 S | 11/2008 | Steele et al. |
| D582,939 S | 12/2008 | Neuhaus |
| 7,470,420 B2 | 12/2008 | Singaram et al. |
| D592,223 S | 5/2009 | Neuhaus |
| 7,615,007 B2 | 11/2009 | Shults et al. |
| D610,065 S | 2/2010 | Gallert |
| 7,751,863 B2 | 7/2010 | Markle et al. |
| D626,143 S | 10/2010 | Karten et al. |
| 7,824,918 B2 | 11/2010 | Suri |
| 7,829,341 B2 | 11/2010 | Gamsey et al. |
| 7,879,024 B2 | 2/2011 | Thorstenson et al. |
| 7,939,664 B2 | 5/2011 | Gamsey et al. |
| 8,178,676 B2 | 5/2012 | Gamsey et al. |
| 8,202,731 B2 | 6/2012 | Suri |
| 2002/0018843 A1 | 2/2002 | Van Antwerp et al. |
| 2002/0026108 A1 | 2/2002 | Colvin, Jr. |
| 2002/0193672 A1 | 12/2002 | Walsh et al. |
| 2003/0013974 A1 | 1/2003 | Natarajan et al. |
| 2003/0028089 A1 | 2/2003 | Galley et al. |
| 2004/0028612 A1 | 2/2004 | Singaram et al. |
| 2004/0072358 A1 | 4/2004 | Ballerstadt |
| 2004/0136924 A1 | 7/2004 | Boyd et al. |
| 2004/0219535 A1 | 11/2004 | Bell et al. |
| 2004/0260158 A1 | 12/2004 | Hogan |
| 2004/0260162 A1 | 12/2004 | Rohleder et al. |
| 2004/0267203 A1 | 12/2004 | Potter et al. |
| 2005/0054975 A1 | 3/2005 | Patel et al. |
| 2005/0090014 A1 | 4/2005 | Rao et al. |
| 2005/0130249 A1 | 6/2005 | Parris et al. |
| 2005/0233465 A1 | 10/2005 | Miller |
| 2005/0241959 A1 | 11/2005 | Ward et al. |
| 2005/0267326 A1 | 12/2005 | Loeb et al. |
| 2006/0083688 A1 | 4/2006 | Singaram et al. |
| 2006/0084854 A1 | 4/2006 | Cho et al. |
| 2006/0105174 A1 | 5/2006 | Aller et al. |
| 2006/0189863 A1 | 8/2006 | Peyser et al. |
| 2006/0189979 A1 | 8/2006 | Esch et al. |
| 2006/0195042 A1 | 8/2006 | Flaherty |
| 2006/0287600 A1 | 12/2006 | McEowen |
| 2007/0060872 A1 | 3/2007 | Hall et al. |
| 2007/0100356 A1 | 5/2007 | Lucatero et al. |
| 2007/0123775 A1 | 5/2007 | Meyer et al. |
| 2007/0175828 A1 | 8/2007 | Goedje et al. |
| 2007/0256477 A1 | 11/2007 | Moor |
| 2008/0001091 A1 | 1/2008 | Kobayashi et al. |
| 2008/0009687 A1 | 1/2008 | Smith et al. |
| 2008/0086042 A1 | 4/2008 | Brister et al. |
| 2008/0154107 A1 | 6/2008 | Jina |
| 2008/0183061 A1 | 7/2008 | Goode et al. |
| 2008/0187655 A1 | 8/2008 | Markle et al. |
| 2008/0188722 A1 | 8/2008 | Markle et al. |
| 2008/0188725 A1 | 8/2008 | Markle et al. |
| 2008/0305009 A1 | 12/2008 | Gamsey et al. |
| 2008/0305506 A1 | 12/2008 | Suri |
| 2009/0018418 A1 | 1/2009 | Markle et al. |
| 2009/0061528 A1 | 3/2009 | Suri |
| 2009/0081803 A1 | 3/2009 | Gamsey et al. |
| 2009/0177143 A1 | 7/2009 | Markle et al. |
| 2009/0264719 A1 | 10/2009 | Markle et al. |
| 2009/0275815 A1 | 11/2009 | Bickoff et al. |
| 2010/0274110 A1 | 10/2010 | Markle |
| 2010/0279424 A1 | 11/2010 | Suri |
| 2010/0312483 A1 | 12/2010 | Peyser |
| 2011/0077477 A1 | 3/2011 | Romey |
| 2011/0105866 A1 | 5/2011 | Markle |
| 2011/0152658 A1 | 6/2011 | Peyser |
| 2011/0171742 A1 | 7/2011 | Gamsey |
| 2011/0224516 A1 | 9/2011 | Romey et al. |
| 2011/0263953 A1 | 10/2011 | Markle |
| 2012/0053427 A1 | 3/2012 | Markle |

FOREIGN PATENT DOCUMENTS

| | | |
|---|---|---|
| DE | 3036868 | 5/1982 |
| DE | 3509262 | 3/1985 |
| DE | 3720736 | 1/1989 |
| DE | 195 02 183 | 8/1996 |
| DE | 298 17 986 | 2/1999 |
| DE | 198 20 808 | 11/1999 |
| EP | 0 073 558 | 3/1983 |
| EP | 0 147 168 | 7/1985 |
| EP | 0 617 977 A1 | 2/1994 |
| EP | 0 596 700 | 5/1994 |
| EP | 0 758 451 B1 | 1/1999 |
| EP | 000760723-0001 | 7/2007 |
| EP | 2217316 | 7/2010 |
| EP | 2 222 686 | 8/2010 |
| EP | 2 147 003 | 4/2011 |
| EP | 2 054 476 | 6/2011 |
| FR | 2 350 831 | 12/1977 |
| FR | 2 624 007 | 6/1989 |
| GB | 1 123 094 | 8/1968 |
| GB | 1 447 163 | 8/1976 |
| GB | 2 048 682 | 12/1980 |
| JP | 53-68249 | 6/1978 |
| JP | 54-13347 | 1/1979 |
| JP | 54-111363 | 8/1979 |
| JP | 54-155856 | 12/1979 |
| JP | 56-116752 | 9/1981 |
| JP | 56-116754 | 9/1981 |
| JP | 58-162921 | 9/1983 |
| JP | 3-52936 | 3/1991 |
| JP | 1332866 | 5/2008 |
| JP | 2009-544729 | 12/2009 |

| | | |
|---|---|---|
| JP | 2010-507711 | 3/2010 |
| JP | 2010-517693 | 5/2010 |
| JP | 2010-518397 | 5/2010 |
| JP | 2010-526599 | 8/2010 |
| JP | 2010-527010 | 8/2010 |
| JP | 2010-535903 | 11/2010 |
| JP | 2011-504399 | 2/2011 |
| JP | 2011-511755 | 4/2011 |
| JP | 5017377 | 6/2012 |
| SU | 6216724 | 8/1978 |
| WO | WO 87/00920 | 2/1987 |
| WO | WO 88/04415 | 6/1988 |
| WO | WO 92/19150 | 11/1992 |
| WO | WO 96/22798 | 8/1996 |
| WO | WO 97/20530 | 6/1997 |
| WO | WO 97/37713 | 10/1997 |
| WO | WO 97/48437 | 12/1997 |
| WO | WO 98/08554 | 3/1998 |
| WO | WO 00/02048 | 1/2000 |
| WO | WO 02/46752 | 6/2002 |
| WO | WO 03/034047 | 4/2003 |
| WO | WO 2004/099778 A1 | 11/2004 |
| WO | WO 2005/090014 A1 | 4/2005 |
| WO | WO 2005/065241 | 7/2005 |
| WO | WO 2006/044973 | 4/2006 |
| WO | WO 2007/067743 | 6/2007 |
| WO | WO 2008/014280 | 1/2008 |
| WO | WO 2008/098011 | 8/2008 |
| WO | WO 2008/098087 | 8/2008 |
| WO | WO 2008/137604 | 11/2008 |
| WO | WO 2008/141241 | 11/2008 |
| WO | WO 2008/141243 | 11/2008 |
| WO | WO 2009/009756 | 1/2009 |
| WO | WO 2009/018426 | 1/2009 |
| WO | WO 2009/021057 | 2/2009 |
| WO | WO 2009/067626 | 5/2009 |
| WO | WO 2009/129186 | 10/2009 |
| WO | WO 2010/141888 | 9/2010 |
| WO | WO 2011/056274 | 5/2011 |
| WO | WO 2011/075710 | 6/2011 |
| WO | WO 2011/075711 | 6/2011 |
| WO | WO 2011/084713 | 7/2011 |
| WO | WO 2011/137178 | 11/2011 |

OTHER PUBLICATIONS

Zhujun, Z., et al. (1984). Analytical Chimica Acta 160:305-309.
Agayn, V. I. and Dr. R. Walt (1993). "Fiber-optic sensor for continuous monitoring of fermentation pH." Biotechnology 72(6):6-9.
Angel, S. M., "Optrodes: Chemically Selective Fiber Optic Sensors," Spectoscopy, Apr. 1987, pp. 38-47.
Badugu R., et al.: "Wavelength-ratiometric near-physiological pH sensors based on 6-aminoquinolinium boronic acid probes" Talanta, Elsevier, Amsterdam, NL, vol. 66, No. 3, Apr. 30, 2005, pp. 569-574, XP004906383 ISSN: 0039-9140, cited in application abstract, conclusion p. 574.
Badugu, R. et al. "Boronic acid fluorescents ensors for monosaccharide signaling based on the 6-methoxyquinolinium heterocyclic nucleus: progress toward noninvasive and continuous glucose monitoring." 2005 Bioorg. Med. Chem. 13 (1):113-119.
Badugu, R. et al. "Fluorescence sensors for monosaccharides based on the 6-methylquinolinium nucleus and boronic acid moiety: potential application to ophthalmic diagnostics." 2005 Talanta 65 (3):762-768.
Bean & Johnson, 54 J. Am. Chem. Soc. 4415 (1932).
Burnett, Peebles & Hageman, 96 Biochemical and Biophysical Research Communications 157 (1980).
Cappuccio, F.E. et al. 2004 "Evaluation of pyranine derivatives in boronic acid based saccharide sensing: Significance of charge interaction between dye and quencher in solution and hydrogel" Journal of Fluorescence 14:521-533.
Cordes, D.B., et al.: "Two-component optical sugar sensing using boronic acid-substituted viologens with anionic fluorescent dyes-Modulated quenching with viologens as a method for monosaccharide detection", Topics in Fluorescence Spectroscopy: vol. 11, Glucose Sensing 2006, Springer, pp. 47-87 (ISBN: 978-0-387-29571-8 p. 76, scheme 3.7).

Dawson, et al., 98 JACS 5996 (1970).
Definition of "cathether" from Webster's Ninth New Collegiate Dictionary, 1990, p. 216.
English Translation of DE 3,720,736.
EPO Office Action re App. No. 07 799 791.4 dated Jan. 29, 2010.
European Examination dated Apr. 1, 2010, re EP Application No. 08 769 266.1-1211.
European Examination Report re Application No. 08 755 267.5, dated Apr. 26, 2010.
Forster, "Intermolecular Energy Transfer and Fluorescence, Annaten der Physik" (1948) pp. 55-75.
Gamoh, et al., 222 Analytica Chimica Acta 201 (1989).
Gamsey, S. et al. 2007 "Boronic acid based bipyridinium salts as tunable receptors for monosaccharides and alpha-hydroxycarboxylates" J Am Chem Soc 129:1278-1286.
Gamsey, Soya et al.: "Continuous glulcose detection using boronic acid-substituted viologens in fluorescent hydrogels: linker effects and extension to fiber optics" Langmuir, ACS, Washington, DC vol. 22, No. 21, Oct. 10, 2006, pp. 9067-9074 (XP002442273 ISSN: 0743-7463, compound (1) schemata 1,2 figure 1).
Gehrich, J. L., D. W. Lubbers, et al. (1986). "Optical fluorescence and its application to an intravascular blood gas monitoring system." IEE TBio-med Eng BME-33: 117-132.
Glazer, 59 Biochemistry 996 (1968).
Glazer, Chemical Abstracts, vol. 68, No. 111805q (1968).
Guilbault, George E., "Practical Fluorescence" (1973), pp. 599-600.
Hakkinen, Lajunen & Purokoski, A Potentiometric Study on the Complex Formation of Lactitol and Maltitol with Some Inorganic Oxyacids in Aqueous Solution, Chemical Abstracts, vol. 110, No. 83116f (1989).
Hakkinen, Purokoski & Lajunen, A Potentiometric Study on the Complex Formation of Germanic Acid and Germanate Ion with Sugar Acids and Disaccharides in Aqueous Solution, Chemical Abstracts, vol. 105, No. 233265s (1986).
Hayashi, et al., 149 Clinica Chimica Acta 149 (1985).
Hirata O. et al. 2002 "Allosteric saccharide sensing by a phenylboronic-acids-appended 5,15- bis(triarylethynyl)porphyrin" J Suprarnolecular Chemistry 2:133-142.
Hirshfeld, "Reabsorption Sensing in Fluorescence Spectroscopy," UCRL Abstract No. 89736 ABST, published by Pittsberg Conference on Scientific Instrumentation, Mar. 1984.
Kirk-Othmer, Encyclopedia of Chemical Technology, 3rd ed., vol. 8, John Wiley and Sons, New York, pp. 201-203 (1979).
Kostov, Y., P. Harms, et al. (2001). "Low-cost microbioreactor for high-throughput bioprocessing." Biotechnol Bioeng 72: 346-352.
Lakowitz et al., :"Optical sensing of glucose using phase-modulation fluorimtry," Analytica Chimica Acta, 271, (1993), 155-164.
Lindner, et al., 473 J. Chromatography 227-240 (1989).
Lutty, G. A. (1978). "The acute intravenous toxicity of stains, dyes, and other fluorescent substances." Toxical Pharmacol. 44: 225-229.
Meadows and Schultz, "Design, manufacture and characterization of an optical fiber glucose affinity sensor based on an homogeneous fluorescence energy transfer assay system," (1993) Anal. Chim. Acta 280: pp. 21-30.
Medtronic, Features of the Guardian REAL-Time Continuous Glucose Monitoring System, Features that fit your diabetes management lifestyle, located at http://www.minimed.com/products/guardian/features.html on Aug. 28, 2007.
Mosbach, Methods in Enzymology, vol. XLIV, 53 (1976).
Niu C.G. et al. "Fluorescence ratiometric pH sensor prepared from covalently immobilized porphyrin and benzothioxanthen e." 2005 Anal. Bioanal. Chem. 383(2):349-357.
Offenbacher, H., O. S. Wolfbeis, et al. (1986). "Fluorescence optical sensors for continuous determination of near-neutral pH values." Sensor Actuator 9: 73-84.
PCT Application No. PCT/US2008/063330.
PCT Application No. PCT/US2008/063332.
PCT International Preliminary Report on Patentabilitu re PCT/US2008/063330 dated Nov. 10, 2009.
PCT International Preliminary Report on Patentability and Written Opinion re PCT/US2008/053097 dated Aug. 11, 2009.
PCT International Preliminary Report on Patentability and Written Opinion re PCT/US2008/072359, dated Feb. 9, 2010.

PCT International Search Report (Declaration of Non-Establishment of ISR) and Written Opinion re PCT/US2009/040379 dated Aug. 4, 2009.
PCT International Search Report and Written Opinion re PCT/US2008/052204, dated May 27, 2008.
PCT International Search Report and Written Opinion re PCT/US2008/053226, dated Oct. 15, 2008.
PCT International Search Report and Written Opinion re PCT/US2008/062303 dated Aug. 14, 2008.
PCT International Search Report and Written Opinion re PCT/US2008/063330 dated Sep. 3, 2008.
PCT International Search Report and Written Opinion re PCT/US2008/069855 dated Apr. 16, 2009.
PCT International Search Report and Written Opinion re PCT/US2008/072359 dated Dec. 15, 2008.
PCT International Search Report and Written Opinion re PCT/US2008/084239 dated Jan. 29, 2009.
PCT International Search Report re PCT/US2007/074255 dated Jul. 8, 2008 in 3 pages.
PCT International Search Report re PCT/US2008/053097 dated Jun. 27, 2008.
PCT Partial International Search Report re PCT/US2008/063332 dated Oct. 20, 2009.
PCT Partial International Search Report re PCT/US2008/072359 dated Oct. 15, 2008.
PCT Partial Search Report re PCT/US2008/053226 dated Jun. 27, 2008.
PCT Report on Patentability and Written Opinion re PCT/US2007/074255 dated Jan. 27, 2009 in 9 pages.
PCT Report on Patentability and Written Opinion re PCT/US2008/063332 dated Nov. 19, 2009.
Purokoski, Lajunen & Hakkinen, A Potentiometric Study on the Complex Formation of Arsenious Acid, Arsenite Ion, Telluric Acid and Tellurate Ion with Sugar Acids and Disaccharides in Aqueous Solution, Chemical Abstracts, vol. 107, No. 122178n (1987).
Roy, et al., J. Inorg. Nucl. Chem., 106 (1957).
Schulman, S. G., S. Chen, et al. (1995). "Dependence of the fluorescence of immobilized 1-hydroxypyrene-3,6,8-trisulfonate on solution pH: extension of the range of applicability of a pH fluorosensor." Anal Chim Acta 304: 165-170.
Seitz, "Chemical Sensors Based on Fiber Optics," Analytical Chemistry, vol. 56, pp. 16a-34a, 1984.
Sharrett, Z. et al. 2008 "Boronic acid-appended bis-viologens as a new family of viologen quenchers for glucose sensing" Tetrahedron Letters 49:300-304.
Snyder, et al., "The Preparation of Some Azo Boronic Acids," 70 J. Am. Chem. Soc. 232 (1948).
Song, A., S. Parus, et al. (1997) "High-performance fiber-optic pH microsensors for practical physiological measurements using a dual-emission sensitive dye." Analytical Chemistry 69: 863-867.
Streitwieser, Jr. & Heathcock, Introduction to Organic Chemistry (1976).
Sturdevant, M. F.: "How Sterilization Changes Long-Term Resin Properties", Plastics Engineering, Jan. 1991, pp. 27-32.
Suri, J. T. et al. 2003 "Continuous glucose sensing with a fluorescent thin-film hydrogel" Angew Chem Int Ed 42:5857-5859.
The Immunoassay Handbook, pp. 1-618, ed. David Wild, Macmillan Press, 1994, United Kingdom.
Turner N.G. et al. "Determination of the pH Gradient Across the Stratum Corneum." 1998 J. Investig. Dermatol. Symp. Proc. Aug. 3(2):110-3.
Udenfreund, "Fluorescence Assay in Biology and Medicine" (1962) pp. 108-109.
Van Kempien & Kreuzer, "A Single-Unit Carbon Dioxide Sensing Microelectrode System," Respiration Physiology, (1975), 23, 371-379.
Vermeer, et al., 37 Tetr. Letters 3255 (1970).
Wang, D. et al. 2001 "Photoluminescence quenching of conjugated macromolecules by bipyridinium derivatives in aqueous media: charge dependence" Langmuir 17:1262-1266.
Wolfbeis, O. S., E. Fuerlinger, et al. (1983). "Fluorimetric analysis. I. Study on fluorescent indicators for measuring near neutral ('physiological') pH values." Fresneius' Z. Anal. Chem. 314(2): 119-124.
Xu, Z., A. Rollins, et al. (1998) "A novel fiber-optic pH sensor incorporating carboxy SNAFL-2 and fluorescent wavelength-ratiometric detection" Journal of Biomedical Materials Research 39:9-15.
Zhang, S., S. Tanaka, et al. (1995). "Fibre-optical sensor based on fluorescent indicator for monitoring physiological pH values." Med Biol Eng Comput 33: 152-156.
Zhujun, Z. and W. R. Seitz (1984). "A fluorescence sensor for quantifying pH in the range from 6.5 to 8.5." Analytical Chimica Acta 160: 47-55.
EPO Exam Report re EP App. No. 08 728 399.0, dated Dec. 7, 2010.
European Examination Report dated Jan. 25, 2012, re EP Application No. 08 729 209.0.
European Examination Report dated Jul. 2, 2012, re EP Application No. 08 729 209.0.
European Examination Report dated May 11, 2010, re EP Application No. 08 729 209.0.
European Examination Report re App. No. 08 797 302.0, dated Jan. 24, 2011.
European Examination Report re App. No. 08 797 302.0, dated Nov. 7, 2011.
European Examination Report re Application No. 08 755 267.5, dated Sep. 14, 2010.
Japanese First Office Action, re JP Application No. 2009-549167, dated Nov. 29, 2011.
Japanese Office Action, re JP Application No. 2009-521962, dated Jul. 31, 2012.
Japanese Office Action, re JP Application No. 2010-507712, dated Jun. 15, 2012.
PCT International Preliminary Report and Written Opinion re PCT/US2009/040379 dated Oct. 19, 2010.
PCT International Preliminary Report on Patentability and Written Opinion date of Issuance Apr. 3, 2012.
PCT International Preliminary Report on Patentability and Written Opinion re PCT Application No. PCT/US2010/061169, dated Jun. 19, 2012.
PCT International Preliminary Report on Patentability and Written Opinion re PCT Application No. PCT/US2010/061173, dated Jun. 19, 2012.
PCT International Preliminary Report on Patentability re PCT/US201 0/037502, dated Dec. 6, 2011.
PCT International Search Report and Report on Patentability re PCT Application No. PCT/US2010/061163, dated (mailed) Jun. 28, 2012.
PCT International Search Report and Written Opinion in App. No. PCT/US2011/028222, dated May 6, 2011, 30 pages.
PCT International Search Report and Written Opinion re App. No. PCT/US 10/61163, dated Mar. 9, 2011.
PCT International Search Report and Written Opinion re App. No. PCT/US10/61169, dated Mar. 1, 2011.
PCT International Search Report and Written Opinion re App. No. PCT/US10/61173, dated Feb. 28, 2011.
PCT International Search Report and Written Opinion re PCT App. No. PCT/US 10/50910, dated Dec. 3, 2010.
PCT International Search Report and Written Opinion re PCT/US2010/037502, dated Aug. 6, 2010.
PCT International Search Report and Written Opinion re PCT/US2011/034167, mailed Jul. 29. 2011.
PCT Preliminary Report re PCT/US2008/084239 dated May 25, 2010.
PCT Search Report and Written Opinion re PCT/US2011/023939, dated Jul. 27, 2011.

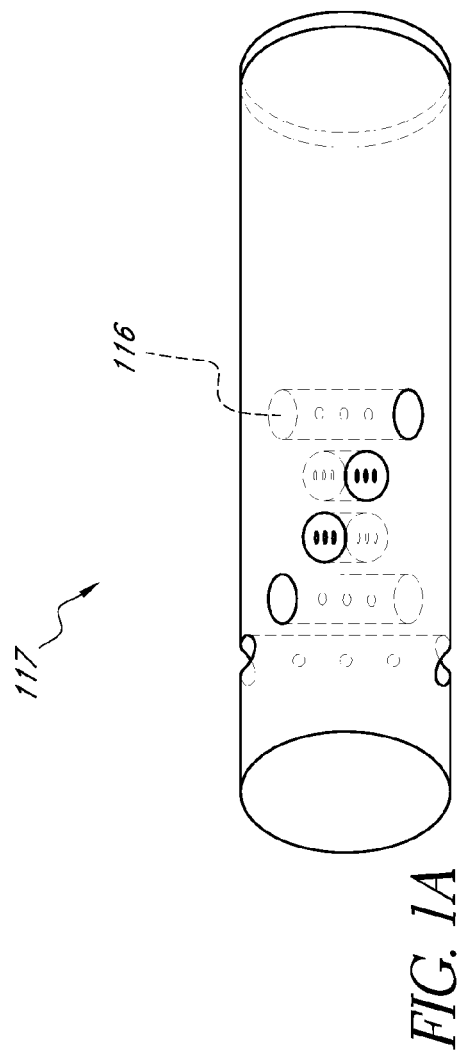
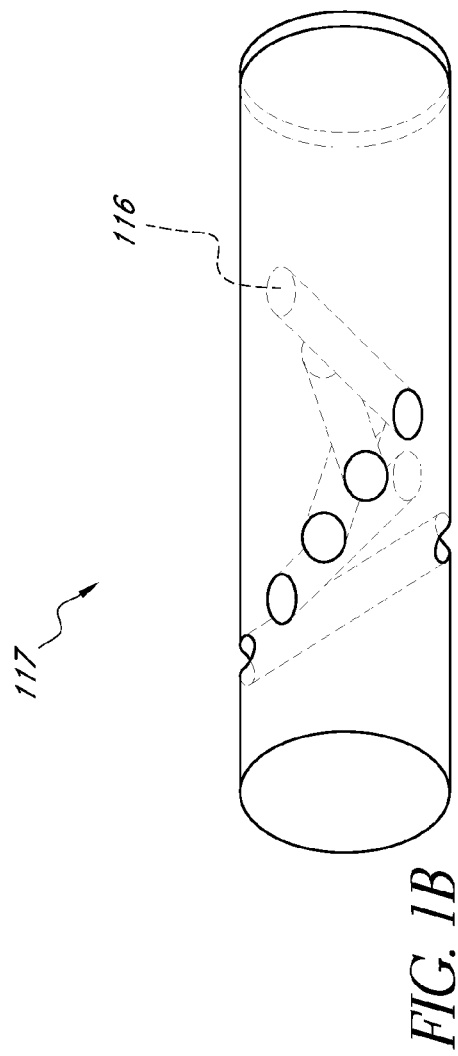
FIG. 1A
FIG. 1B

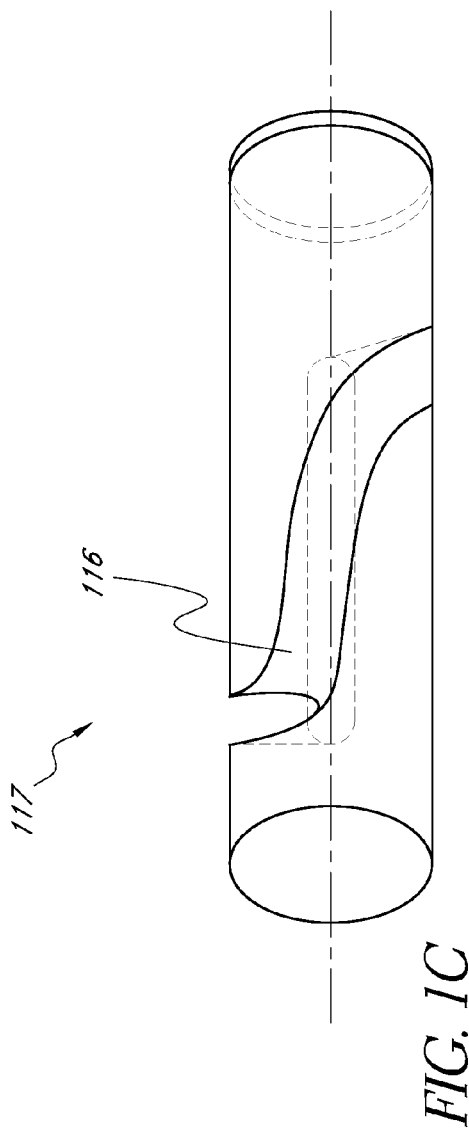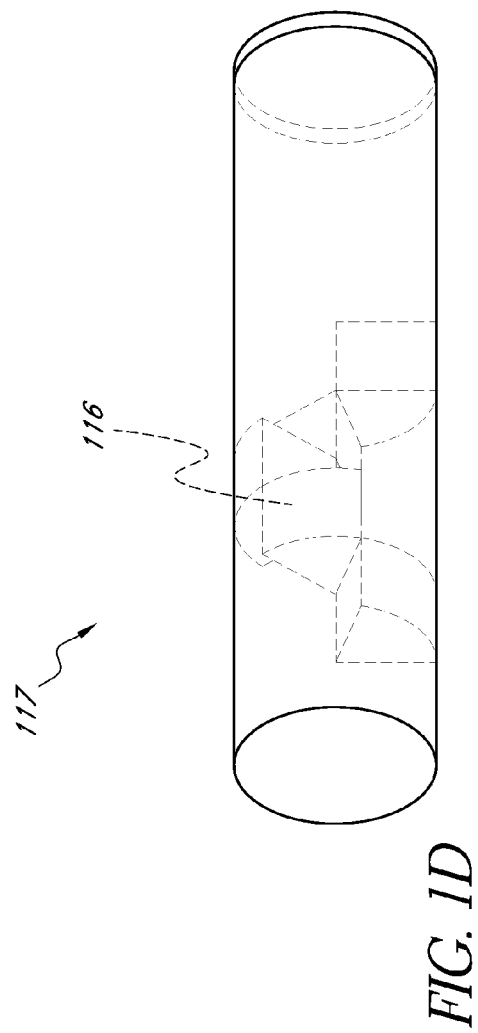
FIG. 1C
FIG. 1D

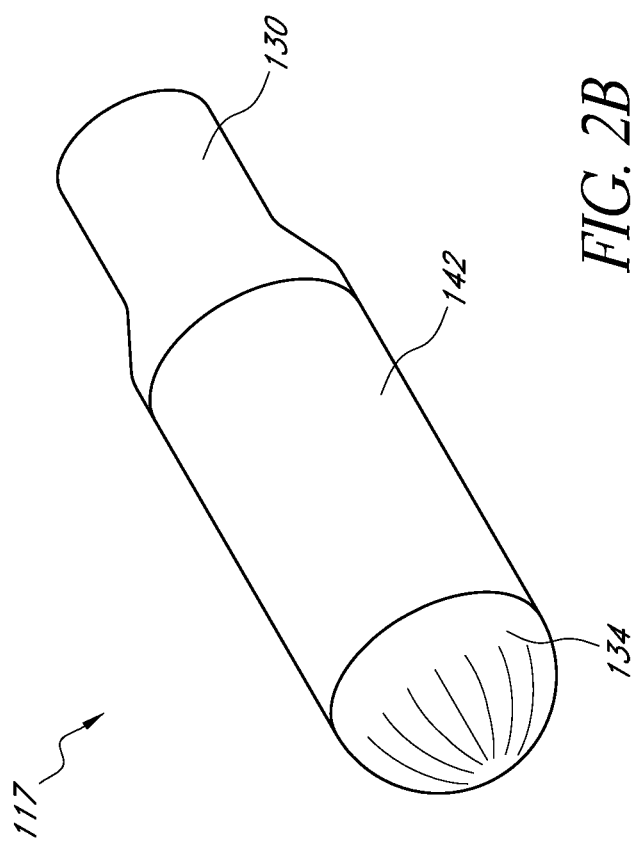

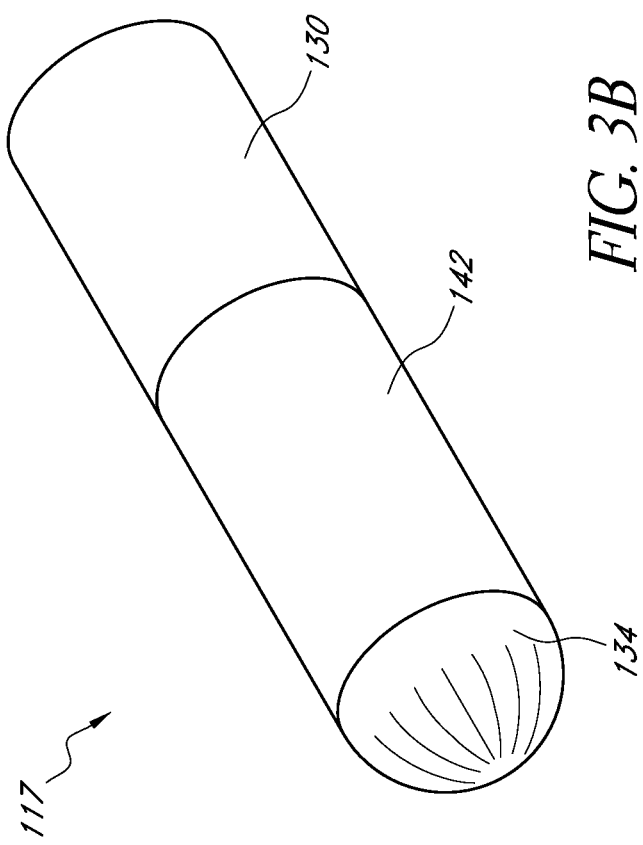

OPTICAL SENSOR CONFIGURATION FOR RATIOMETRIC CORRECTION OF BLOOD GLUCOSE MEASUREMENT

BACKGROUND OF THE INVENTION

1. Field of the Invention

Embodiments of the invention are directed to an optical sensor for detecting an analyte, preferably glucose. In preferred embodiments, the sensor comprises an optical fiber having a fluorescence chemistry disposed along the distal region of the fiber, more preferably located between the distal end of the fiber and an atraumatic tip.

2. Description of the Related Art

Hyperglycemia and insulin resistance are common in critically ill patients, even if such patients have not previously had diabetes. In these situations, glucose levels rise in critically ill patients thereby increasing the risk of damage to a patient's organs. Further, studies have shown that normalization of blood glucose levels with insulin therapy improves the prognosis for such patients, thereby decreasing mortality rates.

More recent scientific evidence confirms that dramatic improvements in the clinical outcome of hospitalized Intensive Care Unit (ICU) patients can result from tight therapeutic control of blood glucose to normal ranges. These studies indicate that Tight Glycemic Control (TGC) of ICU patients may reduce mortality by as much as 40%, and significantly lower complication rates. In these situations, it is necessary to accurately, conveniently and continuously monitor blood sugar in a real-time device specifically designed to meet the challenging needs of the ICU environment. Researchers at Johns Hopkins University estimate that TGC can save as many as 150,000 lives and reduce U.S. healthcare costs by as much as $18 billion annually.

Performing TGC requires continuous and accurate monitoring of a patient's blood glucose levels. Thus, there is a need for a real-time glucose monitoring system that is adapted to meet the needs of ICU patients.

SUMMARY OF THE INVENTION

A sensor for detecting an analyte concentration in a blood vessel is disclosed in accordance with an embodiment of the invention. The sensor comprises: an optical fiber with proximal and distal ends; an atraumatic tip portion with proximal and distal ends, wherein the proximal end of the atraumatic tip portion is separated from the distal end of the optical fiber, such that a gap exists between the atraumatic tip portion and the optical fiber; a rod with proximal and distal ends, wherein the proximal end of the rod is attached to the distal end of the optical fiber, and wherein the distal end of the rod is attached to the proximal end of the atraumatic tip portion, such that the rod traverses the gap and couples the optical fiber to the atraumatic tip portion; a chemical indicator system capable of generating an emission light signal in response to an excitation light signal, wherein the intensity of the emission light signal is related to the analyte concentration, and wherein the chemical indicator system is disposed within the gap; and a selectively permeable membrane disposed over the gap, wherein the sensor is sized for deployment within the blood vessel.

In one variation to the analyte sensor, the chemical indicator system is immobilized within the gap by a hydrogel. In another variation, the sensor further comprises a temperature sensor. The optical fiber preferably has a diameter of between about 0.005 inches and about 0.020 inches. In another variation, the sensor further comprises a reflective region. Preferably, the reflective region comprises a reflective surface of the proximal end of the rod. In one embodiment, the rod may be attached to the optical fiber and atraumatic tip portion by heating. In another embodiment, the rod may be attached to the optical fiber by a reflective or optically clear adhesive.

In variations to the sensor, the shape of the distal end of the atraumatic tip portion may be configured to reduce trauma within the blood vessel. In various embodiments, the shape of the distal end of the atraumatic tip portion may be selected from the group consisting of hemispherical, parabolic, and elliptical. In another variation, the distal end of the atraumatic tip portion is flexible. In another variation, the distal end of the atraumatic tip portion is deformable. The distal end of the atraumatic tip portion may be formed from at least one material selected from the group consisting of plastics, polymers, gels, metals and composites.

The rod may be formed from at least one material selected from the group consisting of metal, metal alloy, plastic, polymer, ceramic, and composite material. In a preferred variation, the rod is formed from stainless steel, titanium, or Nitinol. In one embodiment, the rod is cylindrical. Preferably, the rod diameter is between about 0.002 inches and about 0.010 inches. The rod may be flexible in some embodiments. The rod is stiffer than the optical fiber in some embodiments. In such embodiments, the rod is preferably sufficiently stiff to prevent flexing of the sensor along the gap.

A sensor for detecting an analyte concentration in a blood vessel is disclosed in accordance with another embodiment of the present invention. The sensor comprises: an optical fiber with proximal and distal ends; an atraumatic tip portion with proximal and distal ends, wherein the proximal end of the atraumatic tip portion is separated from the distal end of the optical fiber, such that a gap exists between the atraumatic tip portion and the optical fiber; a hypotube with proximal and distal ends, wherein the proximal end of the hypotube is attached to the distal end of the optical fiber, and wherein the distal end of the hypotube is attached to the proximal end of the atraumatic tip portion, such that the hypotube traverses the gap and couples the optical fiber to the atraumatic tip portion, wherein the hypotube comprises at least one window that opens onto the gap; a chemical indicator system capable of generating an emission light signal in response to an excitation light signal, wherein the intensity of the emission light signal is related to the analyte concentration, and wherein the chemical indicator system is disposed within the gap; and a selectively permeable membrane disposed over the at least one window, wherein the sensor is sized for deployment within the blood vessel. In preferred embodiments, the chemical indicator system is immobilized by a hydrogel within the cavity formed within the hypotube. In further preferred embodiments of the sensor with hypotube, a reflective member is disposed within the sensor. In further preferred embodiments of the sensor with hypotube, a fluorescent member is disposed within the sensor.

A sensor for detecting an analyte concentration in a blood vessel is disclosed according to another embodiment of the present invention. The sensor comprises: an optical fiber with proximal and distal ends; an atraumatic tip portion with proximal and distal ends, wherein the proximal end of the atraumatic tip portion is separated from the distal end of the optical fiber, such that a gap exists between the atraumatic tip portion and the optical fiber; a cage connecting the optical fiber and atraumatic tip portion, wherein the optical fiber is at least partially enclosed within the cage, and wherein the cage has at least one window; a chemical indicator system disposed within the cage, wherein the chemical indicator system is adjacent the window and is separated from analyte by a selectively permeable membrane, and wherein the chemical indicator system is capable of generating an emission light signal in response to an excitation light signal, wherein the intensity of the emission light signal is related to the analyte concentration; and a reference material, wherein the reference material is configured to either reflect a portion of the excitation light signal before the excitation light signal enters the chemical indicator system or to return a second emission light signal, wherein the intensity of the second emission light signal is not related to the analyte concentration.

In another embodiment, a method for measuring glucose concentration is provided. The method comprises transmitting a first light in a first direction through an optical fiber to a glucose sensor, where the glucose sensor comprises a hydrogel cavity having a fluorophore system. At least a portion of the first light is reflected off a reflective surface of the glucose sensor as a second light in a second direction opposite the first direction. A third light is emitted in the second direction. The third light results from the chemical indicator system fluorescing. The method further comprises calculating the glucose concentration, where the glucose concentration is determined by the ratio of the emitted third light to the reflected second light. The ratio is independent of the intensity of the first light.

In another embodiment, a method for measuring glucose concentration is provided. The method comprises transmitting a first light in a first direction through an optical fiber to a glucose sensor, where the glucose sensor comprises a hydrogel cavity having a fluorophore system which is sensitive to glucose as well as a second fluorophore which is glucose insensitive. A second light from the glucose sensitive fluorophore is emitted in a second direction opposite the first direction. A third light from the glucose insensitive fluorophore is also emitted in the second direction. The method further comprises calculating the glucose concentration, where the glucose concentration is determined by the ratio of the emitted second light to the emitted third light. The ratio is independent of the intensity of the first light.

In another embodiment, a system for measuring glucose is provided. The system comprises at least one light source, at least one optical fiber coupled to the light source, any one of the glucose sensors described above coupled to the optical fiber, and a data processing device coupled to the glucose sensor.

In another embodiment, a method for manufacturing a glucose sensor is provided. The method comprises inserting a first end of a rod into an optical fiber, inserting a second end of the rod into an atraumatic tip, surrounding the rod with a hydrogel cavity, and enclosing the hydrogel cavity with a selectively permeable membrane.

In another embodiment, a method for manufacturing a glucose sensor is provided. The method comprises cutting a window in a hypotube, contacting an optical fiber with a first end of the hypotube, and heating the optical fiber, such that the optical fiber swells to fully contact the first end of the rod.

In another embodiment, a sensor for detecting an analyte concentration in a blood vessel is provided. The sensor comprises an optical fiber with a proximal end and a distal end. The distal end of the optical fiber comprises a glucose sensing hydrogel. The glucose sensing hydrogel comprises a first fluorophore, a quencher, and at least one glucose receptor. A reference fiber is adjacent the optical fiber and has a proximal end and a distal end. The distal end of the reference fiber comprises a reference material. The reference material comprises a second fluorophore. A light emitting diode is operably coupled to the glucose fiber and the reference fiber. The light emitting diode sends an excitation light to the glucose fiber and the reference fiber. A glucose signal detector is operatively coupled to the glucose fiber. The glucose signal detector receives a first fluorescent light from the glucose fiber. A reference signal detector is operatively coupled to the reference fiber. The reference signal detector receives a second fluorescent light from the reference fiber.

BRIEF DESCRIPTION OF THE DRAWINGS

FIG. 1A shows a glucose sensor having a series of holes that form a helical configuration.

FIG. 1B shows a glucose sensor having a series of holes drilled or formed at an angle.

FIG. 1C shows a glucose sensor having at least one spiral groove.

FIG. 1D shows a glucose sensor having a series of triangular wedge cut-outs.

FIG. 2B shows a perspective view of the glucose sensor shown in FIG. 2.

FIG. 3B shows a perspective view of the glucose sensor shown in FIG. 4.

DETAILED DESCRIPTION OF THE PREFERRED EMBODIMENT

Figure 2A:
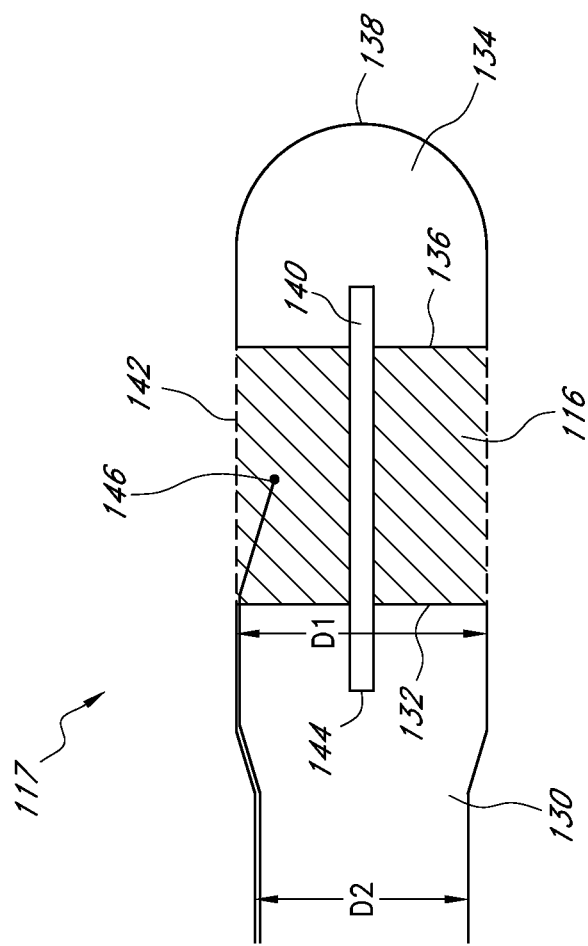
FIG. 2A shows a cross-sectional view of one embodiment of a glucose sensor having a cavity in the distal portion of the sensor and a temperature probe.

Various embodiments of optical systems and methods are disclosed herein for determining blood glucose concentrations. The various embodiments preferably share at least two features. First, they involve exciting a chemical indicator system with an excitation light signal and measuring the emission light signal of the indicator system, wherein the indicator system is in contact with the blood and comprises a fluorescent dye operably coupled to a glucose binding moiety-such that the emission light signal generated by the indicator system upon excitation is related to the blood glucose concentration. Second, they involve correcting the blood glucose concentration measurements from the indicator system for potential artifacts due to the optical system, which artifacts are unrelated to the blood glucose concentration. The correction is performed by ratiometric analysis. More particularly, the ratio of emission light signal to a second light signal that is propagated through the optical system, e.g., the excitation light signal or a separate reference light signal, is used for correcting any non-glucose related contributions of the optical system. Where the excitation light signal is used for the ratiometric correction, the sensor preferably includes a reflective surface, e.g., a minor, located somewhere along the sensor, such that at least a portion of the excitation light which has passed through the optical system is reflected back to a detector. Where a separate reference light signal is used, the reference light signal may either be: (1) generated by a separate light source and reflected back to a detector, or (2) generated as a separate emission light signal from a separate dye disposed somewhere along the sensor. Thus, a glucose sensor in accordance with preferred embodiments of the present invention will comprise either a reflective surface or a second dye adapted to emit a reference light signal.

Various structural configurations have been proposed for holding a chemical indicator system in a position, which is: (1) exposed to the blood, (2) disposed within the excitation light path, and (3) for exposing a chemical indicator system to the blood and, for introducing to the indicator system an excitation light signal, for detecting an emission light signal from the indicator system, and for enabling ratiometric correction of glucose determinations for artifacts of the system optics; see in particular 2008/0188725. More particularly, aspects of the present invention relate to improvements and alternative embodiments for generating a reference light signal (as discussed in 2008/0188725), either through various mirror/reflective surface configurations adapted to return a portion of the excitation light signal back to a detector or through generating a separate emission light signal from a separate dye. Aspects of the present invention relate to new and improved configurations for disposing a chemical indicator system within an interrogation light path, wherein the sensor is more robust and exhibits improved patient tolerance.

Optical glucose sensors, such as those described in U.S. Patent Publ. Nos. 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 12/424,902 (each of which is incorporated herein in its entirety by reference thereto) typically employ a chemical indicator system disposed at the distal end of an optical fiber, wherein the indicator system is maintained in contact with the blood, such that an excitation light signal sent distally down the fiber causes the chemical indicator system to emit a light signal related to the concentration of glucose.

In certain embodiments, an optical glucose measurement system is disclosed for measuring glucose concentration in blood using one or more glucose-sensing chemical indicator systems. Such indicator systems preferably comprise a fluorophore operably coupled to a glucose binding moiety. Preferably, the glucose binding moiety acts as a quencher with respect to the fluorophore (e.g., suppresses the fluorescent emission signal of the fluorophore in response to excitation light when it associates with the fluorophore). In preferred embodiments, as the glucose binding moiety binds glucose (e.g., as glucose concentrations rise), it dissociates from the fluorophore, which then generates a fluorescent emission signal upon excitation. Accordingly, in such embodiments, the higher the glucose concentration, the more glucose bound by the binding moiety, the less quenching, and the higher the fluorescence intensity of the fluorophore upon excitation.

In certain embodiments, the optical glucose measurement system measures glucose concentrations intravascularly and in real-time through the use of such chemical indicator systems. In certain embodiments, the glucose-sensing chemical indicator systems are immobilized in a hydrogel. The hydrogel may be inserted into an optical fiber such that light may be transmitted through the hydrogel while at least a portion of the hydrogel is in contact with blood. The hydrogel is preferably permeable to blood and analytes, specifically glucose. In certain embodiments, the optical fiber together with the hydrogel comprises a glucose sensor that is placed in a mammalian (human or animal) blood vessel.

Examples of glucose-sensing chemical indicator systems and glucose sensor configurations for intravascular glucose monitoring include the optical sensors disclosed in U.S. Pat. Nos. 5,137,033, 5,512,246, 5,503,770, 6,627,177, 7,417,164 and 7,470,420, and U.S. Patent Publ. Nos. 2008/0188722, 2008/0188725, 2008/0187655, 2008/0305009, 2009/0018426, 2009/0018418, and co-pending U.S. patent application Ser. Nos. 11/296,898, 12/187,248, 12/172,059, 12/274,617 and 12/424,902; each of which is incorporated herein in its entirety by reference thereto.

Light may be transmitted into an optical glucose sensor from a light source. In certain embodiments, the light source is a light emitting diode that emits an optical excitation signal. The optical excitation signal excites the fluorophore system (s), such that the fluorophores emit light at an emission wavelength. In certain embodiments, the fluorophore systems are configured to emit an optical emission signal at a first wavelength having an intensity related to the blood glucose concentration in the blood vessel. In certain embodiments, light is directed out of the glucose sensor such that the light is detected by at least one detector. The at least one detector preferably measures the intensity of the optical emission signal, which is related to the glucose concentration present in the blood. Various optical configurations for interrogating glucose-sensing chemical indicator systems with one or more excitation light signals and for detecting one or more emission light signals from the chemical indicator systems may be employed, see e.g., U.S. Patent Appl No. 12/027,158 (published as 2008/0188725); incorporated herein in its entirety by reference thereto.

Glucose Activity and Tight Glycemic Control

While clinicians have used insulin for decades to regulate glucose levels in diabetics and critically ill patients, determining precise dosages remains a problem. Insulin reduces circulating glucose levels through a series of complex interactions involving a number of hormones and cell types. Dosage protocols for insulin attempt to replicate the physiologic secretion of the hormone by the pancreas. However, administering according to fixed times and algorithms based on blood glucose measurements can only crudely approximate the ability of a healthy individual to continuously adjust insulin production in response to the amount of bioavailable glucose and the needs of the body. Thus, to determine the precise amount of insulin that should be administered to maintain a patient's blood glucose at an appropriate level, it is necessary to have near real-time, accurate measurements of the amount of bioavailable glucose circulating in blood.

Unfortunately, most existing methods for determining blood glucose concentrations fail to provide near real-time, accurate measurements of the amount of bioavailable glucose. Clinicians and diabetic patients typically rely on point-of-care testing that seems to measure glucose concentration in plasma, e.g., using glucometers to read test strips that filter separate plasma from cells in a drop of whole blood. While the results can be available quickly, they vary depending on the patient's hematocrit, plasma protein and lipid profiles, etc., and can often be falsely elevated (See e.g., Chakravarthy et al., 2005 "Glucose determination from different vascular compartments by point-of-care testing in critically ill patients" Chest 128(4) October, 2005 Supplement: 220S-221S). More accurate determinations can be obtained by first separating the cellular components of whole blood. However, this requires separation of the plasma from the cellular components of blood, e.g., by centrifugation. Subsequently, isolated plasma must be stored and/or transported and/or diluted prior to analysis. Storage and processing conditions, e.g., temperature, dilution, etc., will almost certainly perturb the in vivo equilibrium between the bound and free (bioavailable) glucose. Consequently, regardless of the technology subsequently employed for measuring plasma glucose concentration (e.g., glucose oxidase, mass spectrometry, etc.), the measured glucose concentration is likely no longer reflective of the amount of bioavailable glucose in vivo. Therefore, it is not feasible to use plasma glucose measurements for near real-time monitoring and adjustment of a patient's glucose level.

Accordingly, in certain embodiments, the preferred glucose sensors described herein measure glucose "activity" as opposed to glucose concentration. More precisely, glucose activity refers to the amount of free glucose per kilogram of water. In some embodiments, glucose activity can be measured directly using glucose sensors, such as the equilibrium, non-consuming optical glucose measurement systems discussed above, which employ a chemical indicator system to quantify the amount of free, bioavailable glucose, which is in equilibrium between the water compartment of blood (i.e., not associated with cells, proteins or lipids, etc.) and the glucose binding moiety/quencher. The discussion of the sensors that follow will often refer to the physical quantity to be measured as an "analyte concentration", "glucose concentration" or simply a "concentration." However, it is to be understood that "concentration" as used herein, refers to both "analyte concentration" as that phrase would be ordinarily used and also to "activity" (in some cases "glucose activity") as that phrase is described above.

Optical Glucose Sensor Configurations

With reference to FIGS. 1A-D, certain prior art embodiments (see US Patent Publication No. 2008/0188725) are illustrated. The glucose sensor 117 in FIG. 1A is an optical fiber with a series holes 116 drilled straight through the sides of the optical fiber. In certain embodiments, the holes 116 are filled with one or more glucose-sensing chemical indicator systems. These holes may be covered with a selectively permeable membrane, wherein the permeability is selected such that the molecules of the chemical indicator system (e.g., fluorophore and quencher) are retained within the cavities, whereas glucose is freely permeable. In certain embodiments, the series of holes 116 that are drilled through the glucose sensor 117 are evenly spaced horizontally and evenly rotated around the sides of the glucose sensor 117 to form a spiral or helical configuration. In certain embodiments, the series of holes are drilled through the diameter of the glucose sensor.

With reference to FIG. 1B, in certain embodiments, the glucose sensor 117 is a solid optical fiber with a series of holes 116 drilled through the sides of the fiber at an angle. In certain embodiments, the series of holes drilled at an angle, which are filled with hydrogel/chemical indicator system, are evenly spaced horizontally and evenly rotated around the sides the glucose sensor 117. With reference to FIG. 1C, in certain embodiments, the optical fiber comprises a groove 116 along the length of the optical fiber, wherein the groove is filled with hydrogel/chemical indicator system. In certain embodiments, the depth of the groove extends to the center of the optical fiber. In certain embodiments, the groove spirals around the optical fiber. In certain embodiments, the groove spirals around the optical fiber to complete at least one rotation. In certain embodiments, the groove spirals around the optical fiber to complete multiple rotations around the optical fiber.

With reference to FIG. 1D, in certain embodiments, the glucose sensor 117 is a solid optical fiber with triangular wedges 116 cut from the fiber. In certain embodiments, the triangular wedge areas are filled with hydrogel/chemical indicator system. In certain embodiments, the triangular wedges cut-outs are evenly spaced horizontally and around the sides of the glucose sensor 117. In certain embodiments, all light traveling in the glucose sensor 117 is transmitted through at least one hole or groove 116 filled with hydrogel/chemical indicator system.

In certain embodiments, as illustrated in FIGS. 2-6, the glucose sensor 117 comprises an optical fiber 130 having a distal end 132, an atraumatic tip portion 134 having a proximal end 136 and a distal end 138, a void or cavity 116 between the distal end 132 of the optical fiber 130 and the proximal end 136 of the atraumatic tip portion 134, and a rod 140 connecting the distal end 132 of the optical fiber 130 to the proximal end 136 of the atraumatic tip portion 134, wherein the rod traverses the void or cavity. In preferred embodiments, molecules of a chemical indicator system are disposed within the void or cavity 116 and immobilized (by covalent bonding or non-covalent interaction) or otherwise associated within hydrogel matrices. See e.g., the chemical indicator systems disclosed in U.S. Pat. Nos. 7,417,164 and 7,470,420. The cavity 116 may be loaded with hydrogel/chemical indicator system by any methods known in the art. In preferred embodiments, the cavity 116 is filled with hydrogel/chemical indicator system in a liquid state. The hydrogel/chemical indicator systems are preferably polymerized in situ, as detailed in co-pending U.S. patent application Ser. No. 12/026,396 (published as 2008/0187655).

In certain embodiments, the rod 140 is attached to the optical fiber 130 and/or atraumatic tip 134 by heating and expanding the optical fiber 130 and atraumatic tip 134 and embedding the rod 140 there between. In certain embodiments, the optical fiber 130 is heated to between about 100° C. and about 160° C., more preferably between about 110° C. and about 140° C. In other embodiments, the optical fiber 130 is first heated and then cooled one or more times. In certain embodiments, the rod 140 is attached to the optical fiber 130 and/or the atraumatic tip 134 by applying an adhesive. In preferred embodiments, the adhesive is biocompatible, such as for example, cyanoacrylates, epoxies, light cure adhesives, silicones, and urethanes. In certain embodiments, after applying the adhesive and joining the rod 140 with the optical fiber 130 and atraumatic tip 134, the adhesive is cured at room temperature, by heating, or by applying UV/visible light. In certain embodiments, the time to fix the rod 140 to the optical fiber 130 and/or atraumatic tip 134 can vary from about 5 seconds to about 60 seconds, from about 15 minutes to about 5 hours, from about 60 seconds to about 10 minutes, or up to about 24 hours.

In some embodiments, the proximal surface of the rod 144 is reflective so that a portion of the excitation light signal (or reference light signal) is reflected proximally down the optical fiber 130 to a detector (not shown). The term rod is used herein to refer to any elongate structural member, regardless of its geometry, configured to connect the atraumatic tip portion to the optical fiber. The rod may be centered coaxially (as illustrated) or off-centered with regard to the cross-section of the fiber and atraumatic tip portion. In some embodiments, there may be more than one rod extending between the fiber and the atraumatic tip portion. Where more than one rod is employed, the rods may be arranged symmetrically or asymmetrically with respect to the cross-section of the fiber and atraumatic tip portion.

Figure 5:
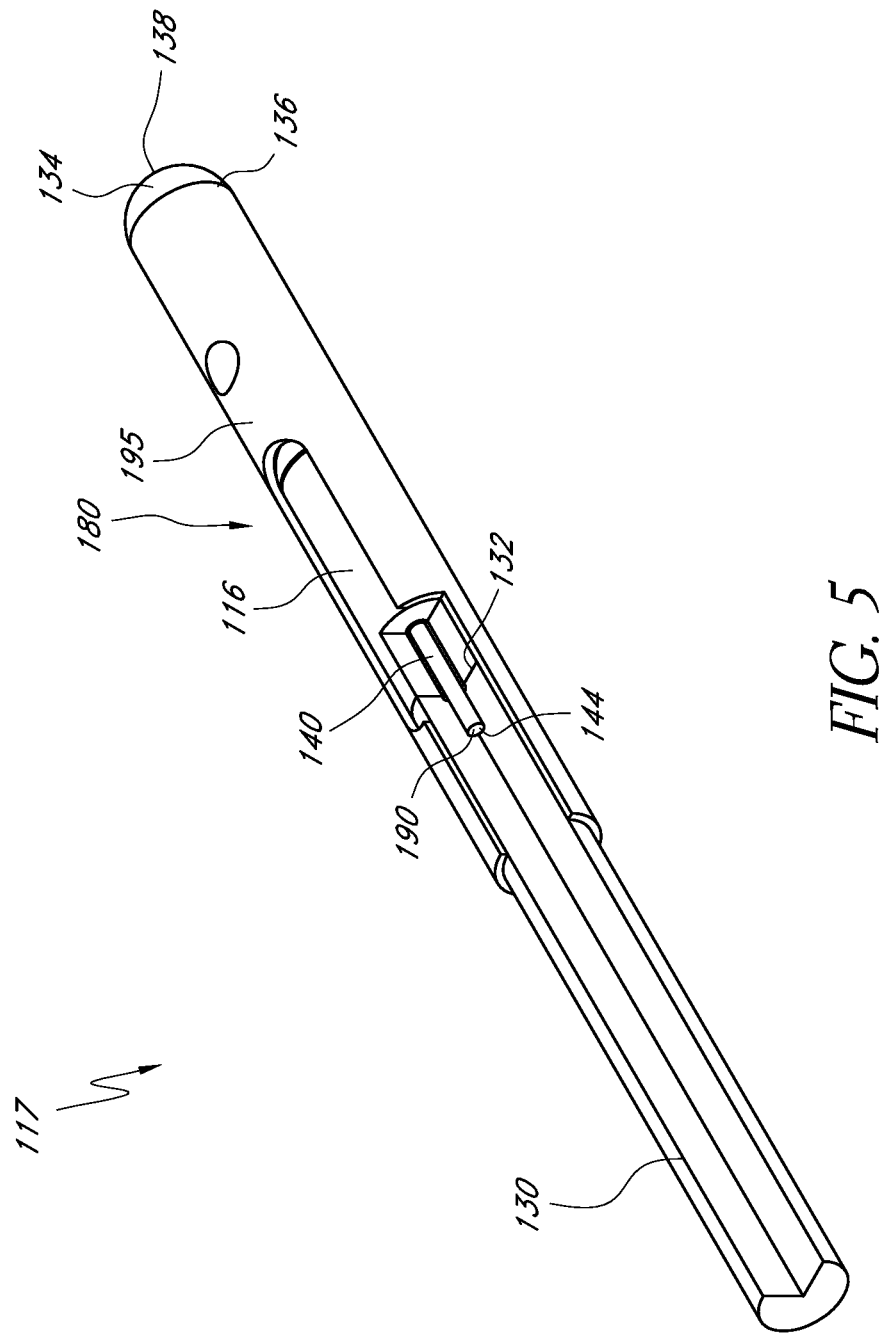
FIG. 5 shows a cross-sectional view of another embodiment of a glucose sensor having a cavity in a distal portion of the sensor enclosed within a cage and an additional reference material.
Figure 6:
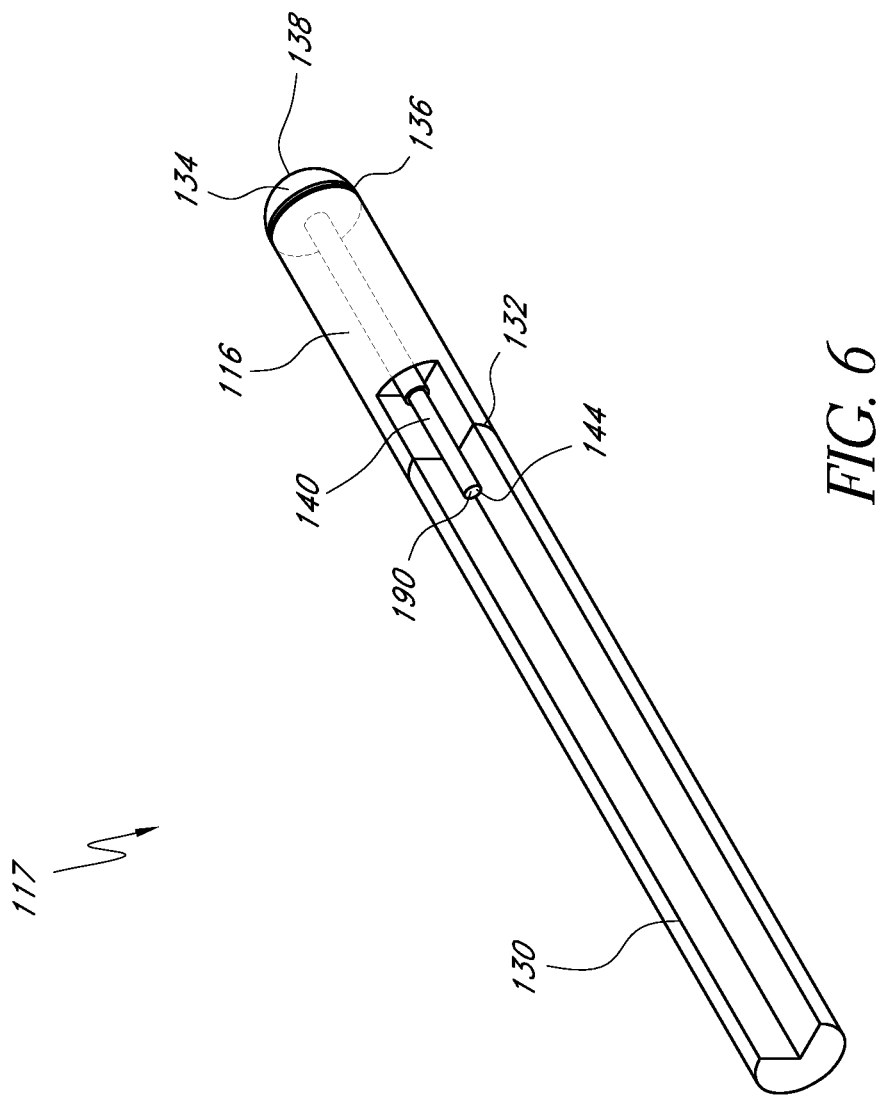
FIG. 6 shows a cross-sectional view of another embodiment of a glucose sensor having a cavity in a distal portion of the sensor and an additional reference material.

In certain embodiments, as illustrated in FIGS. 5 and 6, a reference material 190 may be attached to the proximal surface of the rod 144. The reference material 190 may be reflective (e.g., a minor) and functions similar to embodiments in which the proximal surface of the rod 144 reflects at least a portion of the excitation light signal (or reference light signal) down the optical fiber 130 to a detector (not shown). In other embodiments, the reference material 190 comprises a separate dye indicator system, such as for example a glucose-insensitive fluorescent dye. The excitation light from the optical fiber 130 causes the glucose-insensitive fluorophore to emit a fluorescent light back to a detector (not shown) in order to reference the emission signal from the hydrogel/chemical indicator system. In certain embodiments, the separate dye indicator system is formed of a plastic material, such as for example polycarbonate, polyethylene, or polystyrene, infused with a fluorescent dye configured to emit a separate glucose-insensitive signal.

The hydrogel and glucose-sensing chemical indicator system is disposed within the cavity 116. In preferred embodiments, the hydrogel/chemical indicator system filled cavity 116 is covered by a selectively permeable membrane 142 that allows passage of glucose into and out of the hydrogel/chemical indicator system. Although these embodiments are described using a glucose sensor 117, it should be understood by a person of ordinary skill in the art that the sensor 117 can be modified to measure other analytes by changing, for example, the sensing chemistry, and if necessary, the selectively permeable membrane 142.

In certain embodiments, the selectively permeable membrane 142 is attached to the optical fiber 130 and the atraumatic tip 134 by means of an adhesive. In preferred embodiments, the adhesive is biocompatible, such as for example, cyanoacrylates, epoxies, light cure adhesives, silicones, and urethanes. In certain embodiments, after applying the adhesive and attaching the selectively permeable membrane 142 to the optical fiber 130 and atraumatic tip 134, the adhesive is cured at room temperature, by heating, or by applying UV/visible light. In certain embodiments, the time to adhere the selectively permeable membrane 142 to the optical fiber 130 and/or atraumatic tip 134 can vary from about 5 seconds to about 60 seconds, from about 15 minutes to about 5 hours, from about 60 seconds to about 10 minutes, or up to about 24 hours. In other embodiments, the selectively permeable membrane 142 is pre-fabricated as a sleeve. The sleeve may be slid into place and sealed using an adhesive and/or heated to form-fit the glucose sensor 117. In certain embodiments, the selectively permeable membrane 142 surrounds the entire circumference of the glucose sensor 117. In other embodiments, the selectively permeable membrane 142 covers a window 180 or opening in the glucose sensor 117 exposing the void or cavity 116 to analytes in the blood stream.

In some embodiments, as illustrated in FIGS. 2A and 2B, the sensor 117 comprises a distal portion and a proximal portion. The distal portion of the sensor 117 comprises the atraumatic tip portion 134, the hydrogel/chemical indicator system filled cavity 116, the rod 140, at least the portion of the selectively permeable membrane 142 that covers the cavity 116 and the distal end 132 of the optical fiber 130. The proximal portion of the sensor 117 comprises the proximal portion of the optical fiber 130. In some embodiments, the diameter, D1, of the distal portion of the sensor 117 is greater than the diameter, D2, of the proximal portion of the sensor 117. For example, the diameter D1 of the distal portion of the sensor 117 can be between about 0.0080 inches and 0.020 inches, while the diameter D2 of the proximal portion of the sensor 117 can be between about 0.005 inches to 0.015 inches. In some embodiments, the diameter D1 of the distal portion of the sensor 117 is about 0.012 inches, while the diameter D2 of the proximal portion of the sensor 117 is about 0.010 inches.

In some embodiments, the sensor 117, including the selectively permeable membrane 142, has a smooth surface. The smooth surface can be made for example by the method disclosed in co-pending U.S. patent application Ser. No. 12/026,396 (published as 2008/0187655). In summary, one preferred embodiment of the method comprises filling the cavity 116 with a solution comprising a monomer, crosslinker and an initiator, such as a thermal initiator. After the sensor 117 has been filled, the sensor 117 is dipped into liquid wax, which is allowed to harden around the sensor 117 and selectively permeable membrane 142.

The liquid wax has a melting point that is greater than the thermal initiation temperature. Therefore, in order to reduce the likelihood of initiation during the wax dipping and coating step, the filled sensor 117 can be chilled before the wax dipping and coating step. After the sensor 117 has been coated with wax, the solution in the cavity 116 can be deoxygenated by placing the sensor 117 in a water bath while bubbling an inert gas, such as nitrogen, in the bath.

After deoxygenation, polymerization can be initiated by heating the sensor 117 to a temperature above the thermal initiation temperature, but below the melting point of the wax. Once the solution is substantially polymerized into the hydrogel, the wax can be removed from the sensor by use of a solvent, such as hexane, leaving a sensor 117 with a smooth surface.

Figure 3A:
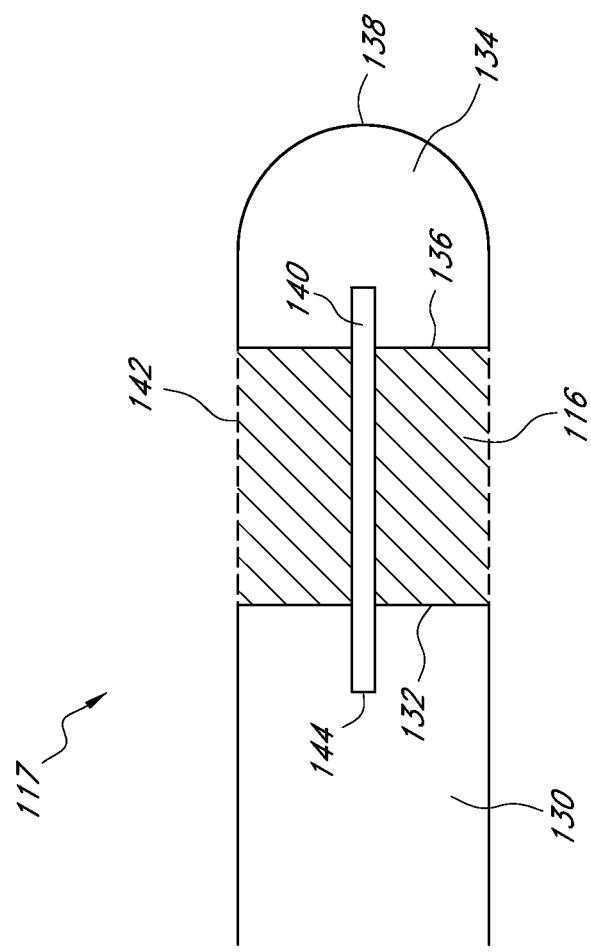
FIG. 3A shows a cross-sectional view of another embodiment of a glucose sensor having a cavity in the distal portion of the sensor.

In some embodiments, as illustrated in FIGS. 3A and 3B, the sensor 117 comprises a distal portion and a proximal portion with substantially the same diameter. In some embodiments, the diameter of the sensor 117 is between about 0.005 inches and 0.020 inches. In other embodiments, the diameter of the sensor 117 is between about 0.008 inches and 0.014 inches. In other embodiments, the diameter of the sensor 117 is about 0.010 inches or about 0.012 inches.

In some embodiments, the rod 140 has a proximal portion that is connected to the distal portion of the optical fiber 130 and a distal portion that is connected to the proximal portion of the atraumatic tip portion 134. The rod 140 can be made of a metal, metal alloy, plastic, polymer, ceramic, composite material or any other material with suitable mechanical properties for connecting the atraumatic tip portion 134 with the distal portion of the optical fiber 130. For example, the rod 140 can be made of stainless steel, titanium or Nitinol. The rod 140 can be cylindrical or noncylindrical, such as a bar with a square, rectangular, oval or oblong cross-section. In some embodiments, the diameter of the rod 140 is generally between about 0.001 to 0.010 inches. In other embodiments, the diameter of the rod 140 is generally between about 0.004 to 0.008 inches. In other embodiments, the diameter of the rod 140 is about 0.001 inches, about 0.002 inches or 0.004 inches. In some embodiments, the diameter of the rod 140 may be less than about 0.001 inches. In some embodiments, the diameter of the rod 140 may be greater than about 0.010 inches. In some embodiments, the length of the rod 140 is generally less than about 0.005 inches. In some embodiments, the length of the rod 140 is between about 0.005 to 0.040 inches. In other embodiments, the length of the rod 140 is generally between about 0.020 to 0.040 inches. In other embodiments, the length of the rod 140 is generally about 0.015 inches. In some embodiments, the length of the rod 140 is generally greater than about 0.005 inches.

The rod 140 adds mechanical stability to the distal portion of the sensor 117. In some embodiments, the rod 140 also adds flexibility to the distal portion of the sensor 117, allowing the atraumatic tip portion 134 to flex back and forth relative to the orientation of the optical fiber 130. The flexibility of the rod 140, and thus the degree which the atraumatic tip portion 134 can flex, can be increased or decreased by decreasing or increasing the diameter of the rod 140. In addition, the flexibility of the rod 140 can be altered by making the rod 140 from a stiff or flexible material.

In some embodiments as illustrated in FIGS. 2A and 3A, a reflective surface 144 is disposed on the proximal end of the rod 140, which is inserted into the optical fiber 130. The reflective surface 144 is capable of reflecting back at least a portion of either reference light or excitation light emitted from the light source. The other end of the rod 140 is inserted into the atraumatic tip portion 134. In certain embodiments, the atraumatic tip portion may be made from a non-reflective material, for example polyethylene (e.g., black polyethylene) or polypropylene. The reference or excitation light that passes though the optical fiber 130 in the region corresponding to the diameter of the rod 140 is reflected off the reflective surface 144 without entering into the hydrogel filled cavity 116; the amount of light entering the hydrogel/chemical indicator system can be controlled by varying the diameter/cross-sectional area of the rod and/or by attaching a minor or other reflective member 190 (illustrated in FIGS. 5 and 6) having a selected cross-sectional area to the proximal end of the rod. The hydrogel filled cavity 116 is preferably covered by a selectively permeable membrane 142, which is at least permeable to glucose. Therefore, the reflected reference or excitation light and the ratio between the reflected and emitted light is independent of the temperature, pH, glucose concentration, and chemistry formulation of the hydrogel filled cavity 116. The ratio between the reflected and emitted light is dependent, however, on the diameter of the rod and the ratio of the diameter of the rod to the area of the sensor. In certain embodiments, the rod 140 is sufficiently stiff to keep the hydrogel filled cavity 116 in a fixed orientation relative to the optical fiber 130 so that any light that is transmitted through the hydrogel cavity 116 is not reflected back to the optical fiber 130.

With regard to FIG. 3B, there is shown a perspective view of the distal region of the sensor 117 illustrated in FIG. 3A. It can be appreciated in the illustrated embodiment that there is no change in sensor diameter from the optical fiber 130, through the membrane 142 covered hydrogel cavity, until the tapered atraumatic distal tip portion 134.

Figure 4:
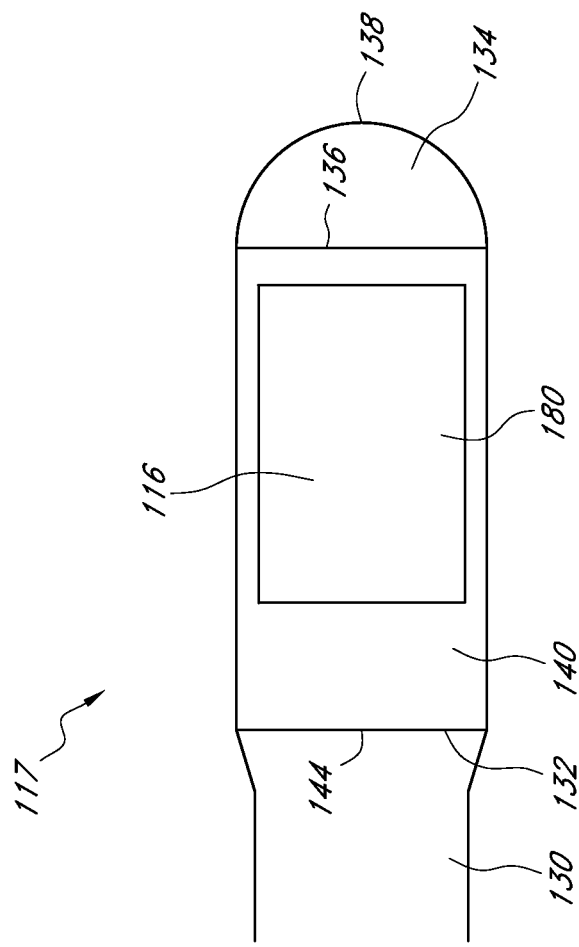
FIG. 4 shows a cross-sectional view of another embodiment of a glucose sensor having a window opening to a cavity in the distal portion of the sensor.

In some embodiments, as shown in FIG. 4, a window 180 is cut into a hypotube 140. The distal end 132 of the optical fiber 130 is inserted onto the reflective surface 144 (e.g., an annular minor) and then heated such that the optical fiber 130 swells to fully contact the reflective surface 144 of the hypotube 140. In certain embodiments, heating the optical fiber 130 is carried out in a glass tube. In other embodiments, heating the optical fiber 130 is carried out in an oven. In still other embodiments, the optical fiber 130 is attached to the hypotube 140 using an adhesive. In preferred embodiments, the adhesive is biocompatible, such as for example, cyanoacrylates, epoxies, light cure adhesives, silicones, and urethanes. In certain embodiments, after applying the adhesive and attaching the optical fiber 130 to the hypotube 140, the adhesive is cured at room temperature, by heating, or by applying UV/visible light. In certain embodiments, the time to adhere the optical fiber 130 to the hypotube 140 can vary from about 5 seconds to about 60 seconds, from about 15 minutes to about 5 hours, from about 60 seconds to about 10 minutes, or up to about 24 hours. Similar methods may be employed for attaching the hypotube 140 to the atraumatic tip 134. Similar to previous embodiments, the reference or excitation light is reflected off the reflective surface 144 without entering the window 180 that opens to the cavity 116 which is filled with hydrogel/chemical indicator system. Therefore, the reflected reference or excitation light and the ratio between the reflected and emitted lights is independent of the temperature, pH, glucose concentration, and hydrogel chemistry. The surface area of the reflective surface can be varied to control the amount of excitation light that enters the hydrogel/chemical indicator system filed cavity 116. The distal end 136 of the hypotube 140, as in previous embodiments, may have a non-reflective surface, such as a black plug made of polyethylene so that light entering the hydrogel/chemical indicator system filled cavity 116 is not reflected back into the optical fiber 130. In some embodiments, the window 180 containing the hydrogel/chemical indicator system filled cavity 116 is covered by a selectively permeable membrane (not shown).

In some embodiments, as illustrated in FIG. 5, the glucose sensor 117 includes a cage 195, as an outer shell, connecting the atraumatic tip 134 with the optical fiber 130. The cage 195 can add mechanical stability to the distal portion of the sensor 117. In some embodiments, the cage 195 also adds flexibility to the distal portion of the sensor 117, allowing the atraumatic tip portion 134 to flex back and forth relative to the orientation of the optical fiber 130. The flexibility of the cage 195, and thus the degree which the atraumatic tip portion 134 can flex, can be increased or decreased by decreasing or increasing the thickness of the cage 195 walls. In addition, the flexibility of the cage 195 can be altered by making the cage 195 from a stiff or flexible material. In certain embodiments, the thickness of the cage 195 walls is about 0.001 inches, about 0.002 inches, or about 0.004 inches. In some embodiments, the thickness of the cage 195 walls may be less than about 0.001 inches. In some embodiments, the thickness of the cage 195 walls may be greater than about 0.010 inches.

In some embodiments, the diameter of the optical fiber 130 may be smaller than the diameter of the interior of the cage 195, allowing the optical fiber 130 to fit within the interior of the cage 195 and abut the void or cavity 116. For example, the diameter of the optical fiber 130 may be between about 0.005 inches and about 0.020 inches, between about 0.008 inches and about 0.014 inches, or between about 0.010 inches and about 0.012 inches. The diameter of the interior of the cage 195 may be about 0.001 inches larger.

In certain embodiments, the cage 195 has a window or opening 180, covered by a selectively permeable membrane 142 (not shown), which allows for at least the transmission of analytes, such a glucose, into the void or cavity 116. In certain preferred embodiments, the void or cavity 116 is filled with a hydrogel/chemical indicator system. A rod 140 may be positioned within the glucose sensor 117 having a reference material 190. As discussed above, the reference material 190 may be a minor for reflecting excitation light from the optical fiber 130 back to a detector (not shown) or a glucose-insensitive fluorescent dye for emitting a glucose-insensitive reference signal back to a detector (not shown). The combination of the cage 195 and the rod 140 may provide a sufficiently rigid structure such that the excitation light which enters the void or cavity 116 remains separate from the light that enters the reference material 190.

In some embodiments, as illustrated in FIG. 6, the glucose sensor 117 does not have a cage 195 surrounding the void or cavity 116. Instead, similar to FIGS. 2A and 3A, the rod 140 connects the optical fiber 130 and atraumatic tip 134, providing structure for the glucose sensor 117, and is surrounded by the void or cavity 116, which in turn is covered by a selectively permeable membrane 142. Similar to FIG. 3A, the diameter of the optical fiber 130 is the same as the diameter of the hydrogel/chemical indicator system encased cavity 116. As discussed with respect to FIG. 5, the rod may have a reference material 190 attached to the proximal surface of the rod 144, which functions as previously discussed.

FIGS. 7-11 illustrate certain embodiments having different configurations for the reference material 190. As discussed previously, the reference material 190 in each of these embodiments may either comprise reflective material to return at least a portion of the excitation light back to a detector (not shown) or a separate dye indicator system to return an emission signal back to a detector (not shown). Similar to previous embodiments, the excitation or reference light is reflected off the reflective surface 190 without entering the cavity 116, which is filled with the hydrogel/chemical indicator system. Likewise, the emitted or reference light from the separate dye indicator system is independent of the glucose concentration. Therefore, the reference light and the ratio between the reference light and emitted glucose concentration dependent lights are independent of the temperature, pH, glucose concentration, and hydrogel chemistry. The surface area, shape, and configuration of the reference material 190 can be varied to control the amount of excitation light that enters the hydrogel/chemical indicator system filed cavity 116. The distal end 136 of the rod or hypotube 140, as in previous embodiments, or reference material 190 may have a non-reflective surface, such as a black plug made of polyethylene so that light entering the hydrogel/chemical indicator system filled cavity 116 is not reflected back into the optical fiber 130.

Figure 7:
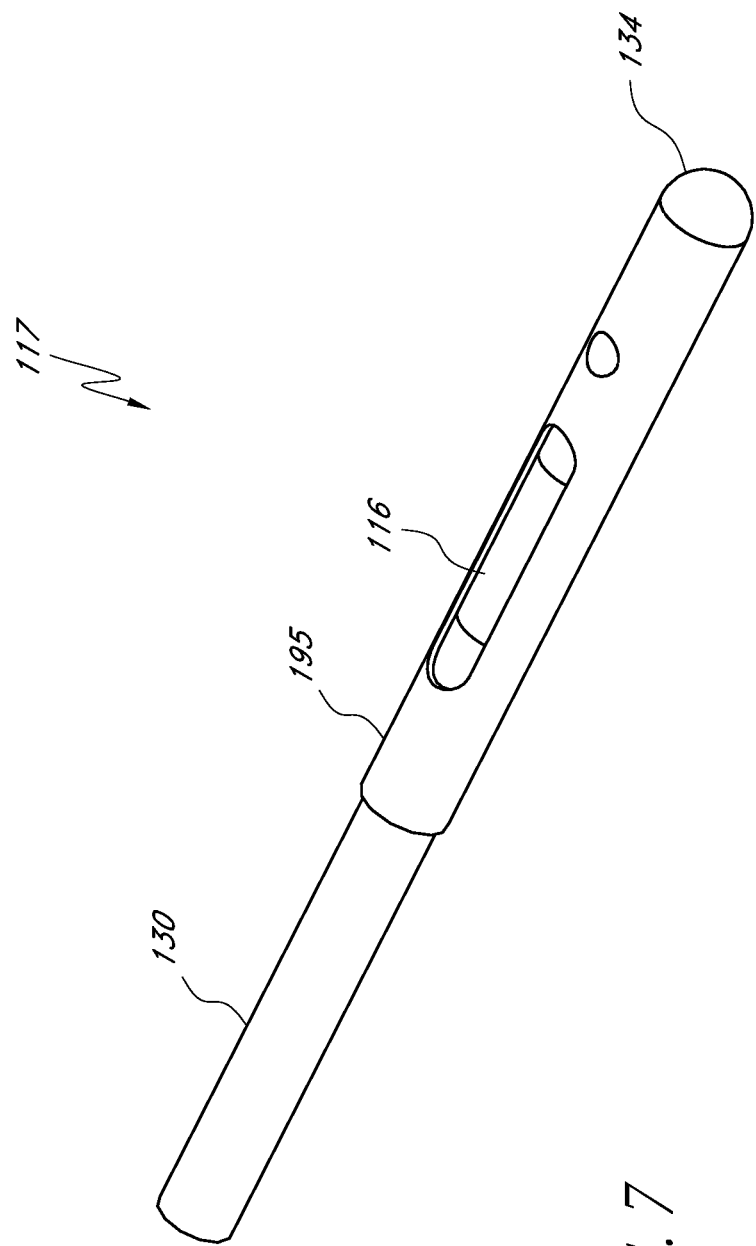
FIG. 7 shows a cross-sectional view of another embodiment of a glucose sensor having a cavity in a distal portion of the sensor enclosed within a cage and a reference material extending to the atraumatic tip.
Figure 8:
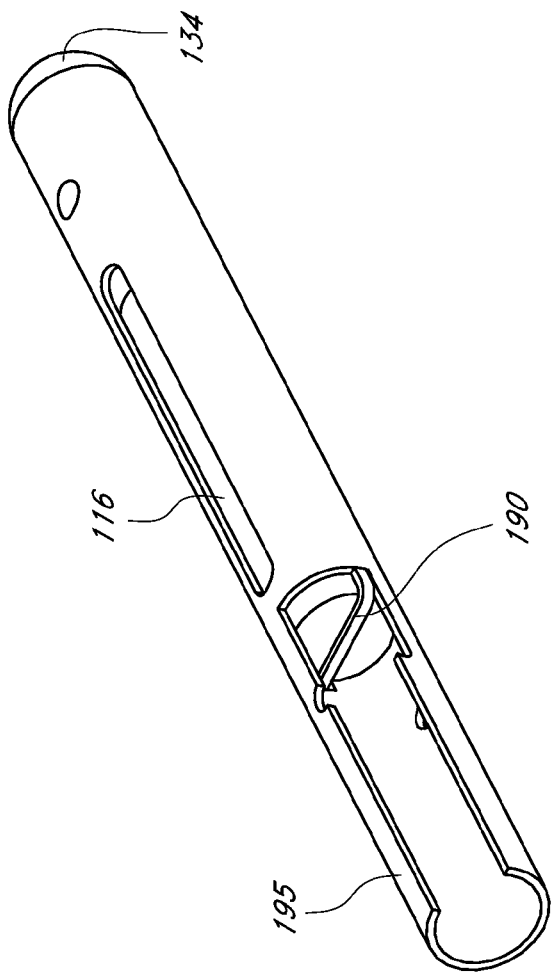
FIG. 8 shows a cross-sectional view of another embodiment of a glucose sensor having a cavity in a distal portion of the sensor enclosed within a cage and a reference material as a bar extending across the diameter of the cage.
Figure 8:
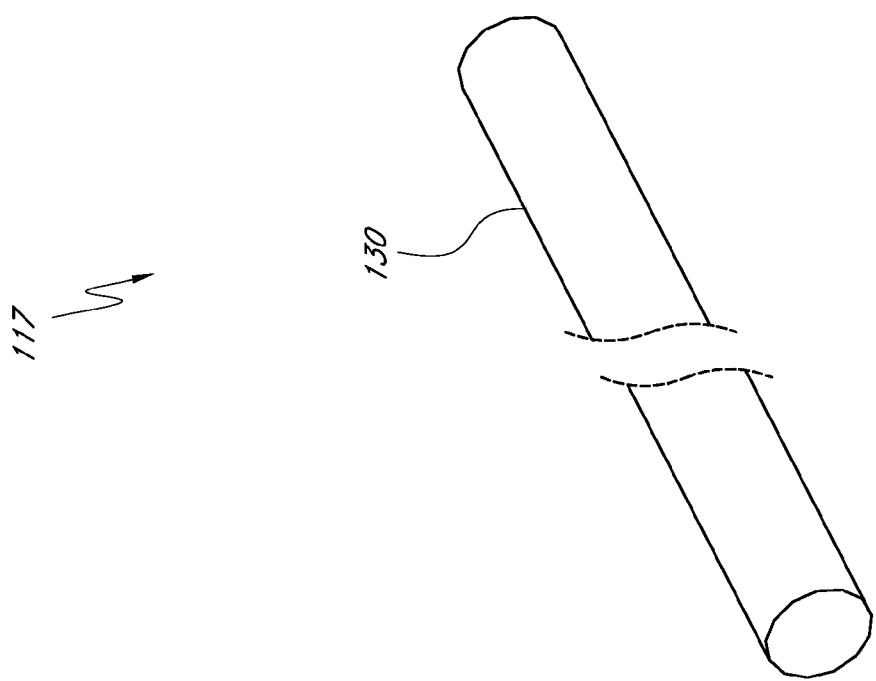

In FIG. 7, the reference material 190 abuts the void or cavity 116 beneath the cage 195 and extends to and comprises the atraumatic tip 134. In certain embodiments, the atraumatic tip 134 is formed of a glucose-insensitive red dye plastic material. In FIG. 8, the reference material 190 is a reflective strip that spans the diameter of the hydrogel-filled cavity 116. The term reflective strip is used herein to refer to any elongate member, regardless of its geometry, width, or thickness that spans at least a cross-section of the glucose sensor 117. The reflective strip 190 may be centered at the diameter of the glucose sensor 117 (as illustrated) or off-centered with regard to the cross-section of the cage 195 or optical fiber 130. In some embodiments, there may be more than one reflective strip in one or more locations within the glucose sensor 117. Where more than one reflective strip is employed, the reflective strip may be arranged symmetrically or asymmetrically with respect to the cross-section of the glucose sensor 117. In certain embodiments, the reflective strip 190 may be between about 0.001 inches and about 0.005 inches wide and between about 0.001 inches and about 0.005 inches thick.

Figure 9:
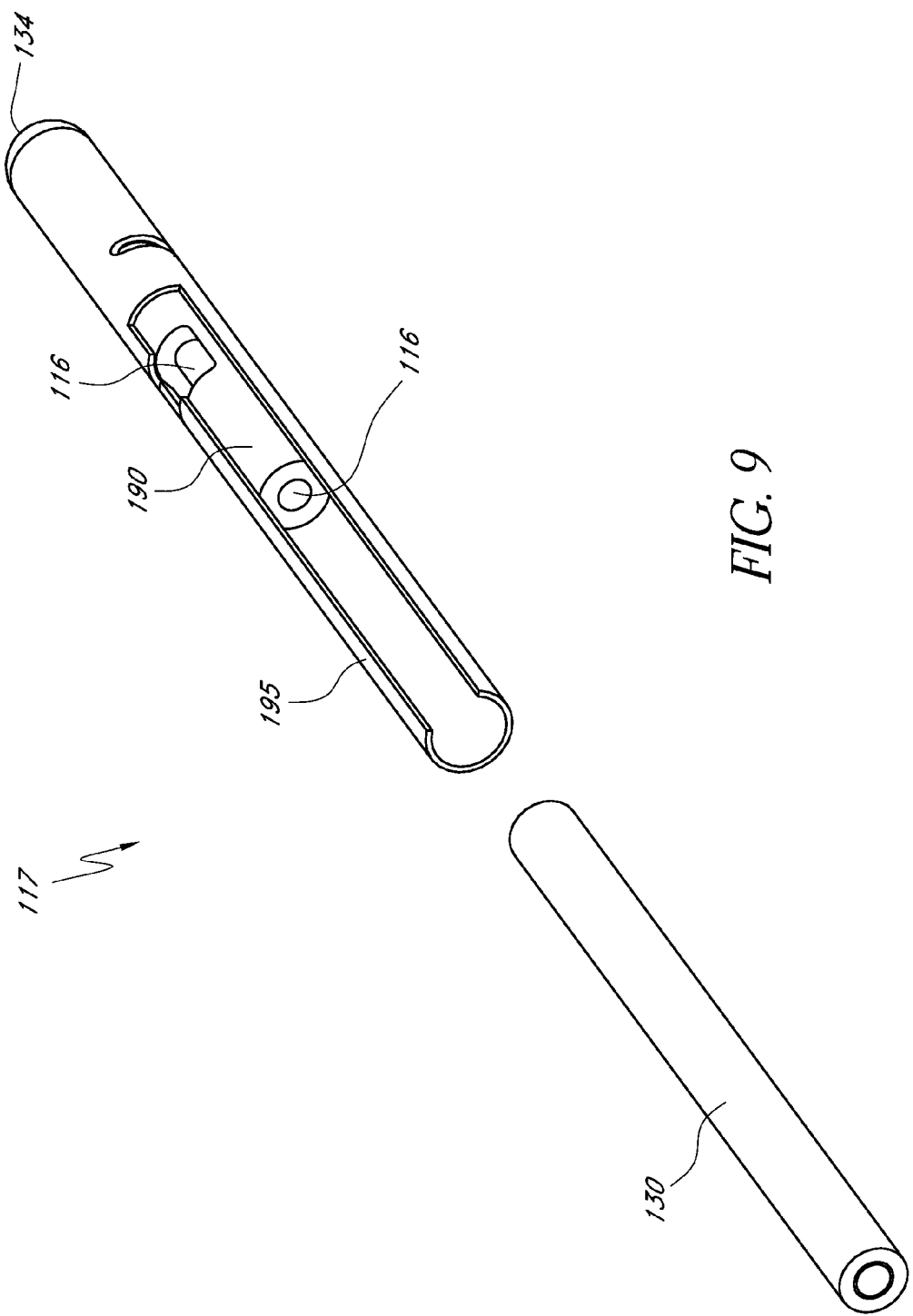
FIG. 9 shows a cross-sectional view of another embodiment of a glucose sensor having a cavity in a distal portion of the sensor enclosed within a reference material, further enclosed within a cage.
Figure 10:
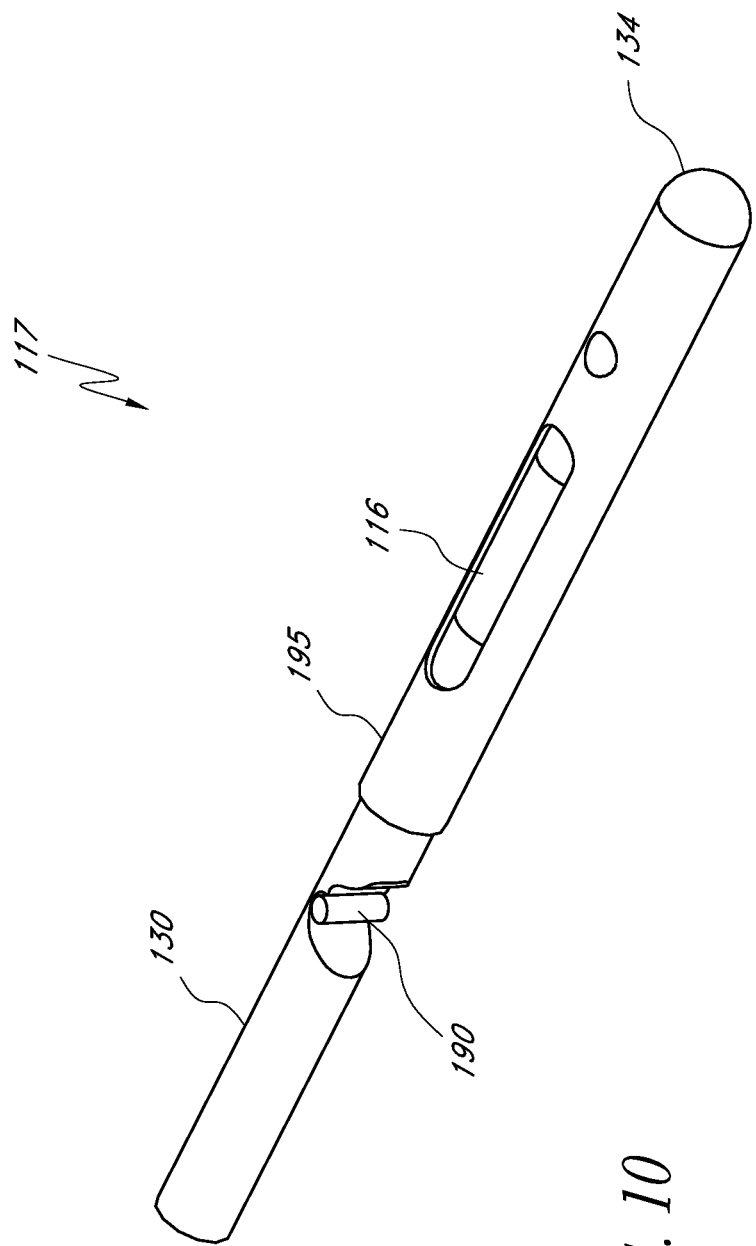
FIG. 10 shows a cross-sectional view of another embodiment of a glucose sensor having a cavity in the distal portion of the sensor enclosed within a cage and a reference material as a bar embedded within the optical fiber.
Figure 11:
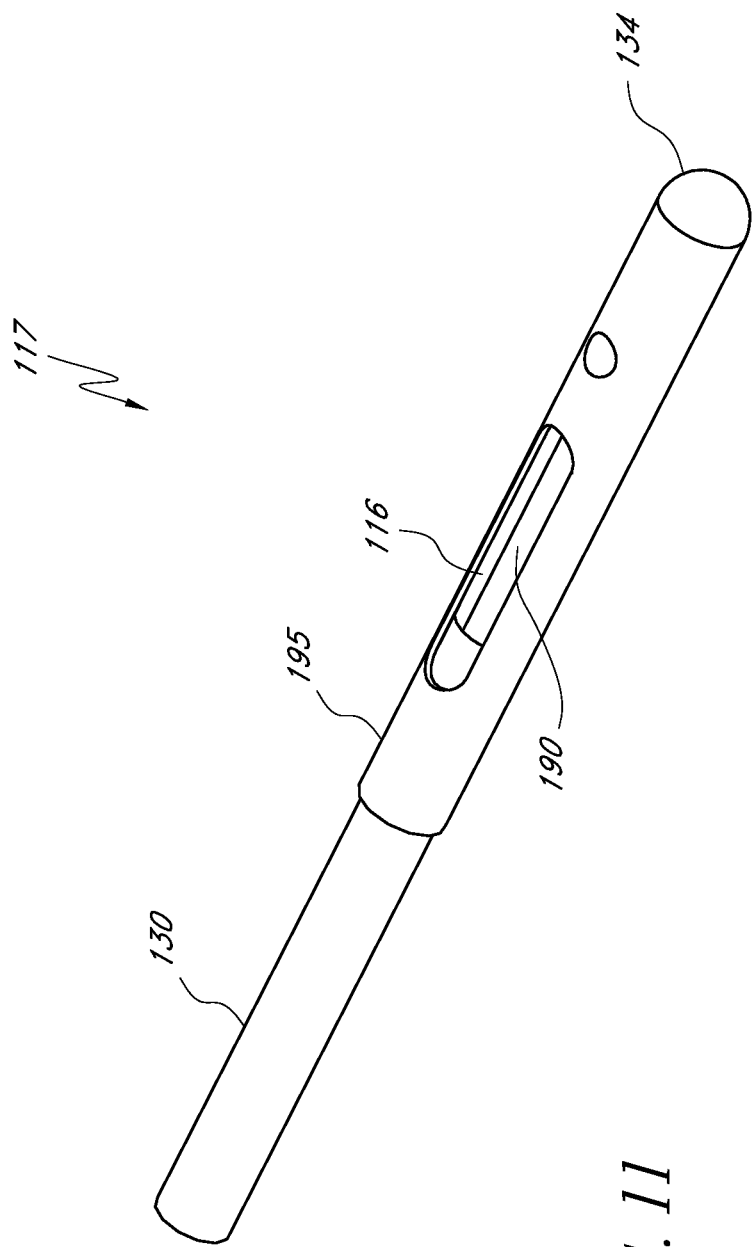
FIG. 11 shows a cross-sectional view of another embodiment of a glucose sensor having a cavity and a reference material side-by-side in the distal portion of the sensor enclosed within a cage.

In FIG. 9, the reference material 190 is disposed within the cage 195 as a hypotube containing the hydrogel-filled cavity 116 and having a reflective surface or annular minor at the proximal surface of the hypotube 144. In certain embodiments, the hypotube 144 has an outer diameter equal to the outer diameter of the optical fiber 130. In FIG. 10, similar to FIG. 8, the reference material 190 is reflective strip, but the reflective strip in FIG. 10 is placed within a hole drilled in the optical fiber 130, rather than the abutting the hydrogel-filled cavity 116. FIG. 11 illustrates an embodiment in which the reference material 190 is located in the cavity 116 and is in a side-by-side configuration with the hydrogel/chemical indicator system.

Figure 12:
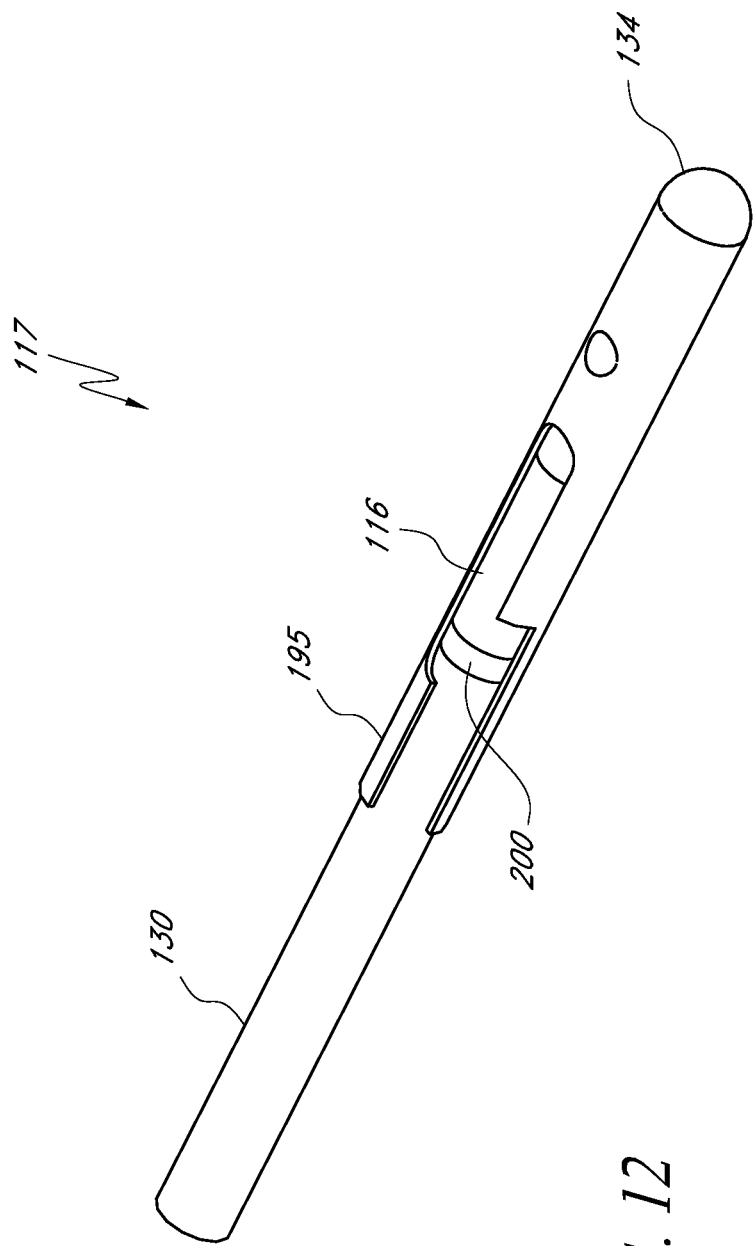
FIG. 12 shows a cross-sectional view of another embodiment of a glucose sensor having a cavity in the distal portion of the sensor enclosed within a cage and a translucent reference material between the optical fiber and cavity.

In certain embodiments, as illustrated in FIG. 12, a reference material 200 comprises a translucent material. In certain embodiments, this translucent material comprises a red dye, such as the glucose-insensitive fluorescent dye discussed previously. The red dye may allow some of the excitation light to be transmitted to the hydrogel-filled cavity 116, may reflect some of the excitation light back to a detector (not shown) before the excitation light reaches the hydrogel-filled cavity 116, and may emit a separate glucose-insensitive signal to a detector (not shown).

A person skilled in the art would readily understand that the above described embodiments, or components of the above described embodiments, may be combined within the scope of the present invention. For example, a glucose sensor may contain one or more structural elements, such as a cage, a hypotube, and/or a rod within the scope of the present invention. In addition, a glucose sensor may contain one or more reference materials, functioning as a reflective surface and/or as a separate dye indicator system, in different locations and configurations within the scope of the present invention.

In some embodiments (see e.g., FIGS. 2-12), the glucose sensor 117 comprises an atraumatic tip portion 134. The atraumatic tip portion 134 has a distal end 138 that is curved and substantially free of sharp edges. In addition, the atraumatic tip portion 134 can be flexible and deformable. The distal end 138 of the atraumatic tip portion 134 can be hemispherical, parabolic, elliptical or curved in any other suitable shape that is reduces the risk of injury to the patient. The atraumatic tip portion 134 can be made from a variety of materials, such as plastics, polymers, gels, metals and composites of the above.

In some embodiments, the glucose sensor 117 includes a temperature sensor or probe 146, such as thermocouple or thermistor (See e.g., FIG. 2A). The temperature sensor 146 can measure the temperature of the hydrogel and glucose sensing chemistry system, and/or the blood when disposed intravascularly. The temperature sensor 146 is particularly preferred when the glucose-sensing chemistry is affected by temperature. For example, in some embodiments, the fluorescence intensity emitted by the fluorophore system is dependent on the temperature of the fluorophore system. By measuring the temperature of the fluorophore system, temperature induced variations in fluorophore fluorescence intensity can be accounted for, allowing for more accurate determination of glucose concentration.

In certain embodiments, the temperature sensor can be a thermistor (as described above with regard to FIG. 2, reference numeral 146, a platinum resistance temperature device ("RTD"), another RTD, a thermocouple, an infrared-based temperature detector, a fluorescence-based temperature sensing element, or other temperature sensing elements with determinable temperature-dependent characteristics.

Devices such as thermistors, platinum RTDs, and other RTDs generally require one or more conductors, such as wires, to conduct the output of the sensor to a receiving unit which converts the output to a temperature signal. The conductors can be bundled with the optical fiber of fluorescence-based glucose sensors, such as those discussed above, or they can be routed separately. In one embodiment, the temperature sensor is placed inside the body, and the receiver is placed outside the body. In another embodiment, the temperature sensor is placed inside the body, and a transmitter, signal processor, etc. is also placed inside the body and is connected to or is a part of the temperature sensor. In preferred embodiments, the temperature sensing element is located at or near the glucose sensing moiety.

In another embodiment, a fluorescence-based temperature sensing technique can be used. Fluorescence-based temperature sensing techniques include those based on fluorescence decay, such as where an excitation light is provided to a phosphor, the excitation light is stopped, and the fluorescence is monitored versus time, with the rate of decrease in fluorescence being related to the temperature of the phosphor. Various techniques, can also include phase measurement and phase angle analysis.

Methods for performing fluorescence-based temperature measurement have been described. See for example, LumaSense Technologies, Inc. (Santa Clara, Calif.), "Fluoroptic Temperature Monitoring," http://www.lumasenseinc.com/technology/fluoroptic_thermometry.html. Fluorescent materials that can be used in fluorescence-based temperature measurement are known to, or readily identified by those having skill in the art.

In some embodiments, the fluorescent material can be surrounded by material which prevents or inhibits chemical interaction between the fluorescent material and blood components. Suitable materials include glass (for example, borosilicate, lime-soda, or other types including those used for fiberoptic cables), polymers (for example, Teflon, fluoropolymers, silicone, latex, polyolefins, polyisoprene, and other rigid and nonrigid polymeric materials), metals (for example, 300 series stainless steel, 400 series stainless steel, nickel, nickel alloys, chromium steels, zirconium and its alloys, titanium and its alloys, as well as other corrosion resistant metals and alloys including exotic metals and alloys), ceramics (for example, ceramic materials related to aluminum oxide, silica and oxide, zirconium, carbides, etc.), and combinations of these.

In some embodiments, the temperature sensor can be positioned within the glucose sensor, or near it. While in one preferred embodiment, the temperature sensor can be positioned as close as possible to (e.g., within) the glucose-sensing chemical indicator system of the glucose sensor, positions some distance away can also be successfully utilized, including those locations where the temperature measured provides an indication of the temperature at the glucose-sensing site(s) within an acceptable error for the use for which the temperature measurement is being made.

In some embodiments, the temperature sensor and/or the leads to the sensor can be isolated from the physiological environment, such as by coating, covering, or encasing the various parts with a material that prevents or inhibits chemical or physical interaction between the temperature sensor and/or its leads and blood components. Chemical interactions that are preferably avoided include corrosion, leaching of chemical species, generation of additional signals (e.g. optical, electrical, etc.) and take-up by the body of materials present in the sensor or leads, whether present from manufacture, corrosion or other means, such as compounds, metals, or ions causing a physiological response in some patients including copper, silver, organic compounds, organometallic compounds, etc.

Physical interactions can include breakage and physical separation (e.g. disconnection and potential loss), signal leakage (e.g. optical; electrical, etc.), signal degradation (including resistance, stray signal detection, noise, capacitance, electrochemical effects, induced voltages, ground loops, etc.). Suitable materials include glass (e.g., borosilicate, lime-soda, as well as other types of glass, such as those used in production of optic fibers), polymers (e.g., Teflon, fluoropolymers, silicone, latex, polyolefins, polyisoprene, acrylics, polycarbonates, and other rigid and nonrigid polymeric materials), metals (e.g., 300 series stainless steel, 400 series stainless steel, nickel, nickel alloys, chromium steels, zirconium and its alloys, titanium and its alloys, as well as other corrosion resistant metals and alloys including exotic metals and alloys), ceramics (e.g., ceramic materials related to aluminum oxide, silica and oxide, zirconium, carbides, etc.), and combinations of these.

Suitable methods for applying for isolating material to the temperature sensor or leads can include any appropriate method, including casting, painting, dipping, gluing, reacting, drawing, depositing, mechanically adhering, encapsulating, etc.

In some embodiments, suitable sizes for temperature sensors that will be incorporated into the glucose sensor include those temperature sensing elements resulting in an overall glucose sensor of between about 0.005 inches and 0.020 inches.

Figure 13:
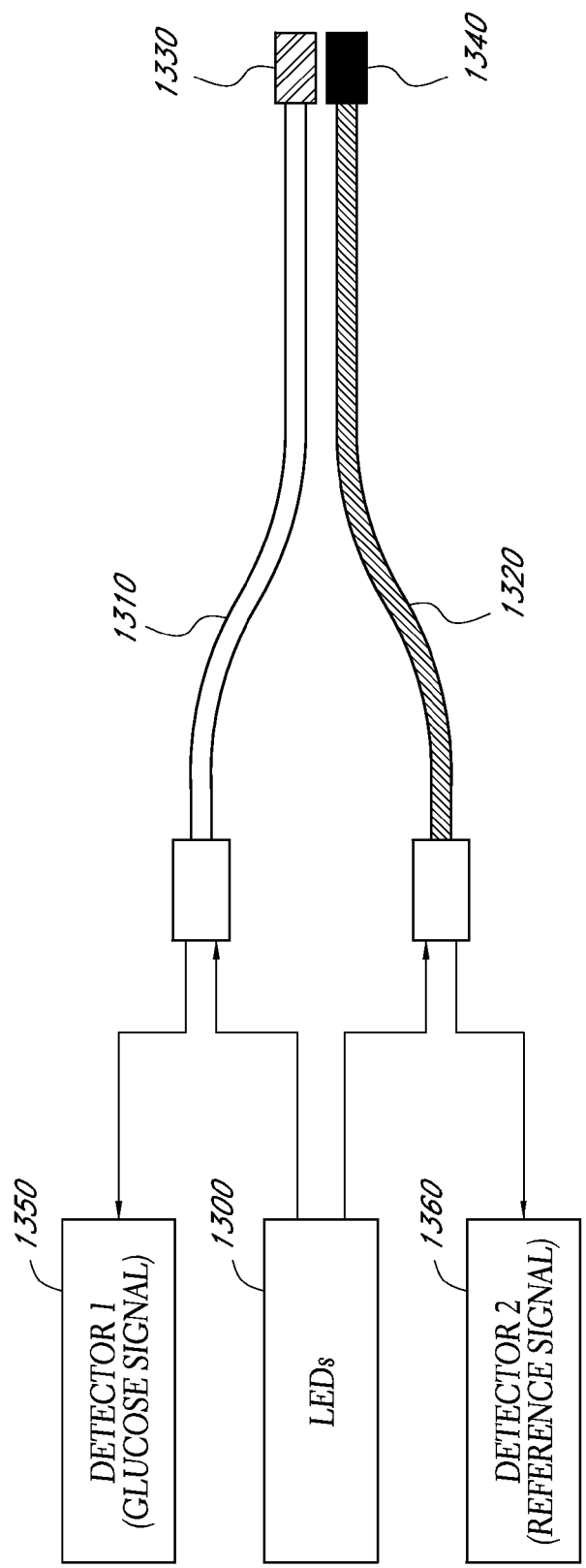
FIG. 13 shows a schematic view of another embodiment of a glucose sensor having a glucose sensing optical fiber adjacent to a reference optical fiber.

FIG. 13 illustrates another embodiment for measuring the glucose concentration in comparison to a reference signal. In this embodiment, a LED source 1300 sends an excitation signal down two separate adjacent optical fibers 1310, 1320. The first optical fiber, or the glucose fiber 1310, has a proximal tip and a distal tip. The distal tip has a glucose sensing hydrogel 1330 which contains a fluorophore or dye, a quencher, and glucose binding receptors. The second optical fiber, or the reference fiber 1320, also has a proximal tip and a distal tip. The distal tip of the reference fiber has a reference material 1340. In certain embodiments, the reference material 1340 contains the same or a different fluorophore or dye, may or may not contain the quencher, but does not contain glucose receptors. In other embodiments, the reference material 1340 has the same exact glucose sensing hydrogel, but it is encased in a glucose impermeable membrane. In both of these embodiments, the reference fiber 1320 emits a fluorescent return signal independent of the glucose concentration.

After the excitation light passes through the glucose fiber 1310 and the reference fiber 1320, the glucose sensing hydrogel 1330 and the reference material 1340 emit fluorescent signals back to two separate detectors, a glucose signal detector 1350 and a reference signal detector 1360, for ratiometric processing. The benefit of the dual fiber configuration is that both fibers 1310, 1320 experience the same external pressure, bending, temperature, and other external factors. In addition, both fibers 1310, 1320 contain substantially the same material in the glucose sensing hydrogel 1330 and reference material 1340. As a result, the ratio of the intensities between the two fibers 1310, 1320, as measured by the detectors 1350, 1360, produce a calibrated glucose signal that removes, inter alia, the effect of the fluctuations in the LED output or altered transmission along the optical fiber, and thereby increase the accuracy in the measurement of the glucose concentration.

Figure 14:
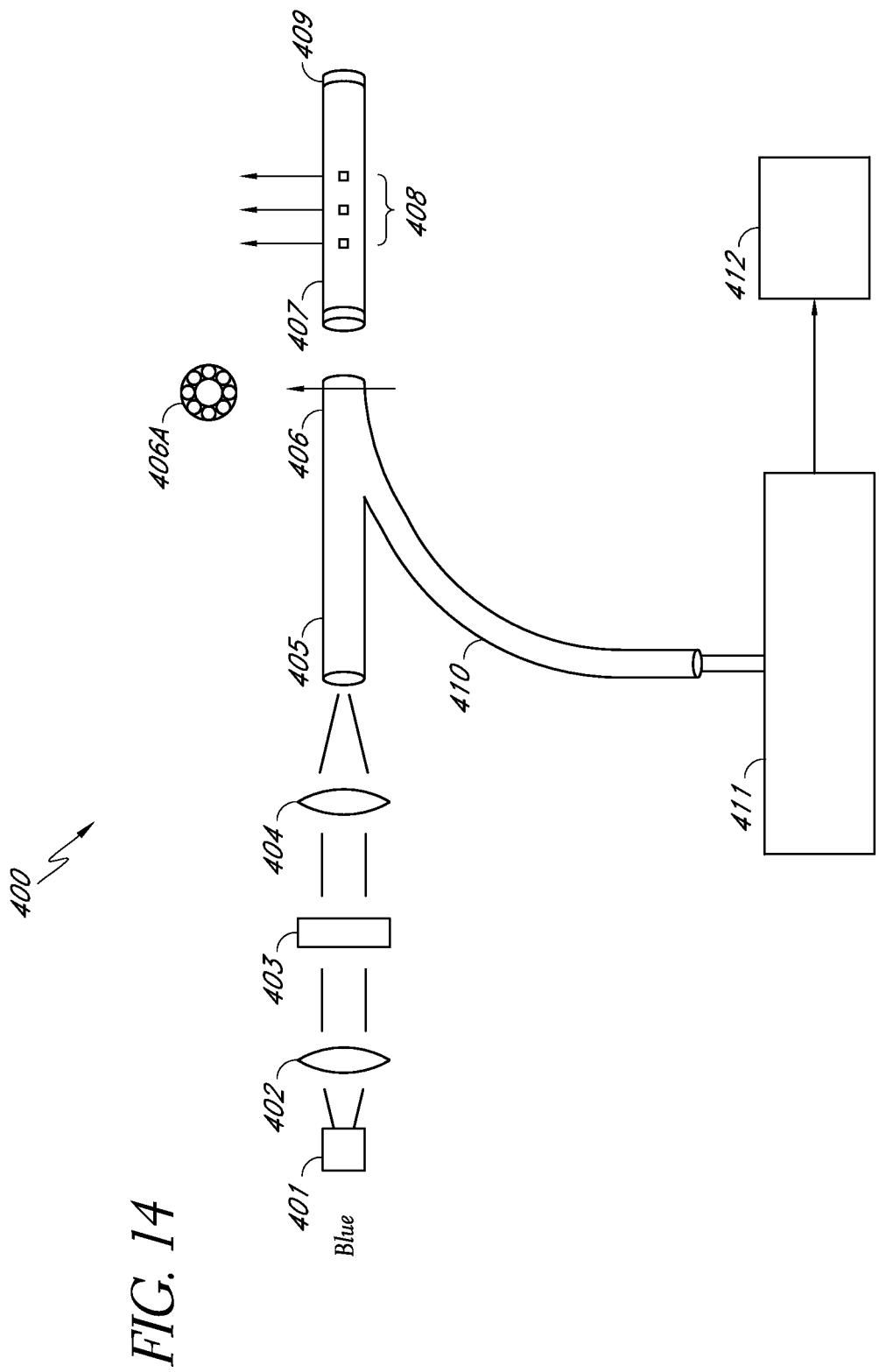
FIG. 14 shows a glucose measurement system comprising one excitation light source, a single exciter-dual emitter fluorophore system, and a microspectrometer and/or spectrometer.

With reference to FIG. 14, in certain embodiments, the light generated by the single light source 401 is transmitted through a optical module comprising a collimator lens 402, an interference filter 403, and/or a focusing lens 404 as described above. The resulting light can be filtered through an interference filter 403. The resulting light can be focused by a focusing lens 404 into an optical fiber 405, which may be a single fiber or a bundle of fibers. The optical fiber 405 can surround optical fiber 410 as both fiber optic lines connect to the first end of the glucose sensor 407. In certain embodiments, a mirror or reflective surface 409 is attached to the second end of the glucose sensor 407. The optical fiber 410 may be a single fiber or a bundle of fibers. The glucose sensor can comprise hydrogels that further comprise a fluorophore system that produces two emission wavelengths, a first emission wavelength and a second emission wavelength. In certain embodiments, the fluorophore system is excited by the light generated by light source 401. In certain embodiments, the optical fiber 410 is connected to a light sensitive module comprising a microspectrometer 411 that measures the entire spectrum of light in the glucose measurement system 400. Data from the microspectrometer 411 can be transmitted to computer 412 for processing. The microspectrometer 411 can allow system 400 to simultaneously measure the excitation light intensity as well as both emission light intensities. Ratiometric calculations may be employed to substantially eliminate or reduce non-glucose related factors affecting the intensity of the measured emission light and measured excitation light (as detailed in US Patent Publication No. 2008/0188725; incorporated herein in its entirety by reference thereto). The measured emission light can be divided by the measured excitation light, wherein such calculations substantially eliminate or reduce non-glucose related factors affecting the intensity of the lights.

In certain preferred embodiments, the fluorophore dye may be selected such that it exists in distinguishable acid and base conformations, each of which emit at a distinct wavelength, and wherein the relative proportion of acid and base forms depend on the pH. The ratio of intensities of the acid and base emissions can be used to determine the pH of the blood (as detailed in US Patent Publication No. 2008/0188722; incorporated herein in its entirety by reference thereto). The ratio of the acid or base emission intensity over the excitation light can be used to determine the level of glucose in the blood. Of course in a variation to this single exciter-dual emitter fluorophore system, one could employ a single exciter-single emitter for detection of glucose concentration without simultaneous ratiometric determination of pH. Indeed, a great variety of design options are available (see e.g., US Patent Publication Nos. 2008/0188725 and 2008/0188722), wherein the chemical indicator and optical systems may be selected based on the preferred use.

Glucose-Sensing Chemical Indicator Systems

In certain embodiments, the hydrogels are associated with a plurality of fluorophore systems. In certain embodiments, the fluorophore systems comprise a quencher with a glucose receptor site. In certain embodiments, when there is no glucose present to bind with the glucose receptor, the quencher prevents the fluorophore system from emitting light when the dye is excited by an excitation light. In certain embodiments, when there is glucose present to bind with the glucose receptor, the quencher allows the fluorophore system to emit light when the dye is excited by an excitation light.

In certain embodiments, the emission produced by the fluorophore system may vary with the pH (as well as the temperature) of the solution (for example, blood), such that different excitation wavelengths (one exciting the acid form of the fluorophore and the other the base form of the fluorophore) produce different emissions signals. In preferred embodiments, the ratio of the emission signal from the acid form of the fluorophore over the emission signal from the base form of the fluorophore is related to the pH level of the blood. In certain embodiments, an interference filter is employed to ensure that the two excitation lights are exciting only one form (the acid form or the base form) of the fluorophore. Chemical indicator systems, hardware configurations and methods for determining both pH and glucose based on ratiometric determination are described in detail in co-pending U.S. application Ser. Nos. 11/671,880 (published as 2008/0188722) and 12/027,158 (published as 2008/0188725); incorporated herein in their entirety by reference thereto.

The indicator system (also referred to herein as a fluorophore system) can comprise a fluorophore operably coupled to a quencher. In certain embodiments, the fluorophore system comprises a polymer matrix comprising a fluorophore susceptible to quenching by a viologen, a viologen quencher with quenching efficacy dependent on glucose concentration, and a glucose permeable polymer, wherein said matrix is in contact with blood in vivo. Preferably the fluorophore is a fluorescent organic dye, the quencher is a boronic acid functionalized viologen, and the matrix is a hydrogel.

"Fluorophore" refers to a substance that when illuminated by light at a particular wavelength emits light at a longer wavelength; i.e. it fluoresces. Fluorophores include but are not limited to organic dyes, organometallic compounds, metal chelates, fluorescent conjugated polymers, quantum dots or nanoparticles and combinations of the above. Fluorophores may be discrete moieties or substituents attached to a polymer.

Fluorophores that may be used in preferred embodiments are capable of being excited by light of wavelength at or greater than about 400 nm, with a Stokes shift large enough that the excitation and emission wavelengths are separable by at least 10 nm. In some embodiments, the separation between the excitation and emission wavelengths may be equal to or greater than about 30 nm. These fluorophores are preferably susceptible to quenching by electron acceptor molecules, such as viologens, and are resistant to photo-bleaching. They are also preferably stable against photo-oxidation, hydrolysis and biodegradation.

In some embodiments, the fluorophore may be a discrete compound.

In some embodiments, the fluorophore may be a pendant group or a chain unit in a water-soluble or water-dispersible polymer having molecular weight of about 10,000 daltons or greater, forming a dye-polymer unit. In one embodiment, such dye-polymer unit may also be non-covalently associated with a water-insoluble polymer matrix $M^1$ and is physically immobilized within the polymer matrix $M^1$, wherein $M^1$ is permeable to or in contact with an analyte solution. In another embodiment, the dye on the dye-polymer unit may be negatively charged, and the dye-polymer unit may be immobilized as a complex with a cationic water-soluble polymer, wherein said complex is permeable to or in contact with the analyte solution. In one embodiment, the dye may be one of the polymeric derivatives of hydroxypyrene trisulfonic acid. The polymeric dyes may be water-soluble, water-swellable or dispersible in water. In some embodiments, the polymeric dyes may also be cross-linked. In preferred embodiments, the dye has a negative charge.

In other embodiments, the dye molecule may be covalently bonded to the water-insoluble polymer matrix $M^1$, wherein said $M^1$ is permeable to or in contact with the analyte solution. The dye molecule bonded to $M^1$ may form a structure $M^1$-$L^1$-Dye. $L^1$ is a hydrolytically stable covalent linker that covalently connects the sensing moiety to the polymer or matrix. Examples of $L^1$ include lower alkylene (e.g., $C_1$-$C_8$ alkylene), optionally terminated with or interrupted by one or more divalent connecting groups selected from sulfonamide (—$SO_2$NH—), amide —(C=O)N—, ester —(C=O)—O—, ether. —O—, sulfide —S—, sulfone (—$SO_2$—), phenylene —$C_6H_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) and the like, or a combination thereof. In one embodiment, the dye is bonded to a polymer matrix through the sulfonamide functional groups.

In one preferred embodiment, the fluorophore may be HPTS-CysMA (structure illustrated below); see U.S. Pat. No. 7,417,164, incorporated in its entirety herein by reference thereto.

tionality of being able to bind analyte and being able to modulate the apparent concentration of the fluorophore (e.g., detected as a change in emission signal intensity) in a manner related to the amount of analyte binding. In preferred embodiments, the analyte binding moiety is associated with a quencher. "Quencher" refers to a compound that reduces the emission of a fluorophore when in its presence. Quencher (Q) is selected from a discrete compound, a reactive intermediate which is convertible to a second discrete compound or to a polymerizable compound or Q is a pendant group or chain unit in a polymer prepared from said reactive intermediate or polymerizable compound, which polymer is water-soluble or dispersible or is an insoluble polymer, said polymer is optionally crosslinked.

In one example, the moiety that provides glucose recognition in the embodiments is an aromatic boronic acid. The boronic acid is covalently bonded to a conjugated nitrogen-containing heterocyclic aromatic bis-onium structure (e.g., a viologen). "Viologen" refers generally to compounds having the basic structure of a nitrogen containing conjugated N-substituted heterocyclic aromatic bis-onium salt, such as 2,2'-, 3,3'- or 4,4'-N,N' bis-(benzyl) bipyridium dihalide (i.e., dichloride, bromide chloride), etc. Viologen also includes the substituted phenanthroline compounds. The boronic acid substituted quencher preferably has a pKa of between about 4 and 9, and reacts reversibly with glucose in aqueous media at a pH from about 6.8 to 7.8 to form boronate esters. The extent of reaction is related to glucose concentration in the medium. Formation of a boronate ester diminishes quenching of the

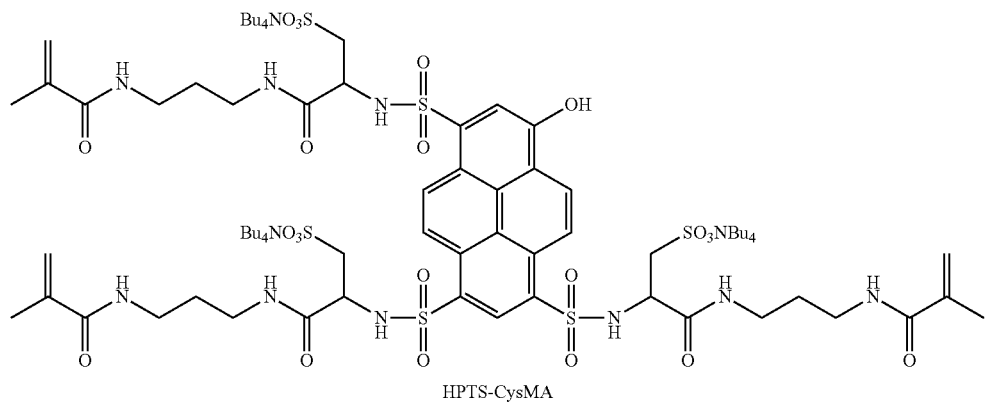

HPTS-CysMA

Of course, in some embodiments, substitutions other than Cys-MA on the HPTS core are consistent with aspects of the present invention, as long as the substitutions are negatively charged and have a polymerizable group. Either L or D stereoisomers of cysteine may be used. In some embodiments, only one or two of the sulfonic acids may be substituted. Likewise, in variations to HPTS-CysMA shown above, other counterions besides $NBu_4^+$ may be used, including positively charged metals, e.g., $Na^+$. In other variations, the sulfonic acid groups may be replaced with e.g., phosphoric, carboxylic, etc. functional groups.

Fluorescent dyes, including HPTS and its derivatives are known and many have been used in analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; each of which is incorporated herein in its entirety by reference thereto.

In accordance with broad aspects of the present invention, the analyte binding moiety provides the at least dual funcfluorophore by the viologen resulting in an increase in fluorescence dependent on glucose concentration. A useful bis-onium salt is compatible with the analyte solution and capable of producing a detectable change in the fluorescent emission of the dye in the presence of the analyte to be detected.

Bis-onium salts in the embodiments of this invention are prepared from conjugated heterocyclic aromatic di-nitrogen compounds. The conjugated heterocyclic aromatic di-nitrogen compounds are selected from dipyridyls, dipyridyl ethylenes, dipyridyl phenylenes, phenanthrolines, and diazafluorenes, wherein the nitrogen atoms are in a different aromatic ring and are able to form an onium salt. It is understood that all isomers of said conjugated heterocyclic aromatic di-nitrogen compounds in which both nitrogens can be substituted are useful in this invention. In one embodiment, the quencher may be one of the bis-onium salts derived from 3,3'-dipyridyl, 4,4'-dipyridyl and 4,7-phenanthroline.

In some embodiments, the viologen-boronic acid adduct may be a discrete compound having a molecular weight of about 400 daltons or greater. In other embodiments, it may also be a pendant group or a chain unit of a water-soluble or water-dispersible polymer with a molecular weight greater than about 10,000 daltons. In one embodiment, the quencher-polymer unit may be non-covalently associated with a polymer matrix and is physically immobilized therein. In yet another embodiment, the quencher-polymer unit may be immobilized as a complex with a negatively charge water-soluble polymer.

In other embodiments, the viologen-boronic acid moiety may be a pendant group or a chain unit in a crosslinked, hydrophilic polymer or hydrogel sufficiently permeable to the analyte (e.g., glucose) to allow equilibrium to be established.

In other embodiments, the quencher may be covalently bonded to a second water-insoluble polymer matrix $M^2$, which can be represented by the structure $M^2$-$L^2$-Q. $L^2$ is a linker selected from the group consisting of a lower alkylene (e.g., $C_1$-$C_8$ alkylene), sulfonamide, amide, quaternary ammonium, pyridinium, ester, ether, sulfide, sulfone, phenylene, urea, thiourea, urethane, amine, and a combination thereof. The quencher may be linked to $M^2$ at one or two sites in some embodiments.

In certain embodiments, at least one quencher precursor is used to attach the quenching moiety to at least one polymer. For example, aromatic groups may be used to functionalize a viologen with combinations of boronic acid groups and reactive groups. In certain embodiments, this process includes attaching an aromatic group to each of the two nitrogens in the dipyridyl core of the viologen. At least one boronic acid group, a reactive group, or a combination of the two are then attached to each aromatic group, such that the groups attached to each of the two nitrogens on the dipyridyl core of the viologen may either be the same or different. Certain combinations of the functionalized viologen quenching moiety are described as follows:

a) a first aromatic group having a pendent reactive group is attached to the first nitrogen and a second aromatic group having at least one pendent boronic group is attached to the second nitrogen;

b) one or more boronic acid groups are attached to a first aromatic group, which is attached to the first nitrogen, and one boronic acid group and a reactive group are attached to a second aromatic group, which second aromatic group is attached to the second nitrogen;

c) one boronic acid group and a reactive group are attached to a first aromatic group, which first aromatic group is attached to the first nitrogen, and one boronic acid group and a reactive group are attached to a second aromatic group, which is attached to the second nitrogen; and d) one boronic acid group is attached to an aromatic group, which aromatic group is attached to each of the two nitrogens, and a reactive group is attached to a carbon in a heteroaromatic ring in the heteroaromatic centrally located group.

Preferred embodiments comprise two boronic acid moieties and one polymerizable group or coupling group wherein the aromatic group is a benzyl substituent bonded to the nitrogen and the boronic acid groups are attached to the benzyl ring and may be in the ortho- meta- or para-positions.

In one preferred embodiment, the quencher precursor (before incorporation into a hydrogel) may be 3,3'-oBBV (structure illustrated below); see U.S. Pat. No. 7,470,420, incorporated in its entirety herein by reference thereto.

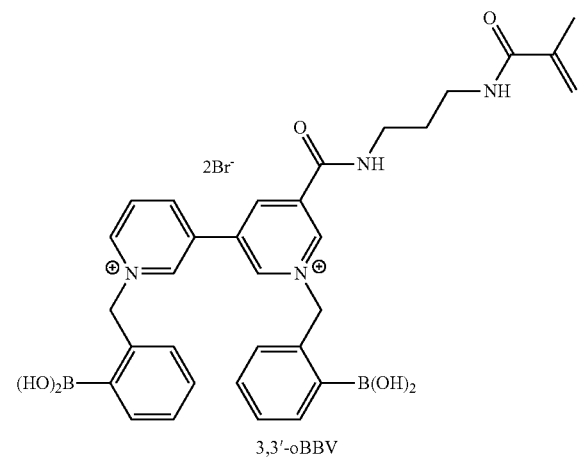 [SMILES: C=C(C)C(=O)NCCCNC(=O)c1cc(-c2ccc[n+](Cc3ccccc3B(O)O)c2)c[n+](Cc2ccccc2B(O)O)c1]

3,3'-oBBV

The quencher precursor 3,3'-oBBV may be used with HPTS-CysMA to make hydrogels in accordance with preferred aspects of the invention.

Other indicator chemistries, such as those disclosed in U.S. Pat. No. 5,176,882 to Gray et al. and Pat. No. 5,137,833 to Russell, can also be used in accordance with embodiments of the present invention; both of which are incorporated herein in their entireties by reference thereto. In some embodiments, an indicator system may comprise an analyte binding protein operably coupled to a fluorophore, such as the indicator systems and glucose binding proteins disclosed in U.S. Pat. Nos. 6,197,534, 6,227,627, 6,521,447, 6,855,556, 7,064,103, 7,316,909, 7,326,538, 7,345,160, and 7,496,392, U.S. Patent Application Publication Nos. 2003/0232383, 2005/0059097, 2005/0282225, 2009/0104714, 2008/0311675, 2008/0261255, 2007/0136825, 2007/0207498, and 2009/0048430, and PCT International Publication Nos. WO 2009/021052, WO 2009/036070, WO 2009/021026, WO 2009/021039, WO 2003/060464, and WO 2008/072338 which are hereby incorporated by reference herein in their entireties.

For in vivo applications, the sensor is used in a moving stream of physiological fluid which contains one or more polyhydroxyl organic compounds or is implanted in tissue such as muscle which contains said compounds. Therefore, it is preferred that none of the sensing moieties escape from the sensor assembly. Thus, for use in vivo, the sensing components are preferably part of an organic polymer sensing assembly. Soluble dyes and quenchers can be confined by a selectively permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include ethylene dimethacrylate, PEGDMA, trimethylolpropane triacrylate, and the like. The ratios of monomers are chosen to optimize network properties including permeability, swelling index, and gel strength using principles well established in the art. In one embodiment, the dye moiety is derived from an ethylenically unsaturated derivative of a dye molecule, such as 8-acetoxypyrene-1,3,6-N,N',N''-tris(methacrylamidopropylsulfonamide), the quencher moiety is derived from an ethylenically unsaturated viologen such as 4-N-(benzyl-3-boronic acid)-4'-N'-(benzyl-4-ethenyl)-dipyridinium dihalide (m-SBBV) and the matrix is made from HEMA and PEGDMA. The concentration of dye is chosen to optimize emission intensity. The ratio of quencher to dye is adjusted to provide sufficient quenching to produce the desired measurable signal.

In some embodiments, a monolithic hydrogel is formed by a condensation polymerization. For example, acetoxy pyrene trisulfonyl chloride is reacted with an excess of PEG diamine to obtain a tris-(amino PEG) adduct dissolved in the unreacted diamine. A solution of excess trimesoyl chloride and an acid acceptor is reacted with 4-N-(benzyl-3-boronic acid)-4'-N'-(2 hydroxyethyl) bipyridinium dihalide to obtain an acid chloride functional ester of the viologen. The two reactive mixtures are brought into contact with each other and allowed to react to form the hydrogel, e.g. by casting a thin film of one mixture and dipping it into the other.

In other embodiments, multi-component hydrogels wherein the dye is incorporated in one component and the quencher in another are preferred for making the sensor of this invention. Further, these systems are optionally molecularly imprinted to enhance interaction between components and to provide selectivity for glucose over other polyhydroxy analytes. Preferably, the multicomponent system is an interpenetrating polymer network (IPN) or a semi-interpenetrating polymer network (semi-IPN).

The IPN polymers are typically made by sequential polymerization. First, a network comprising the quencher is formed. The network is then swollen with a mixture of monomers including the dye monomer and a second polymerization is carried out to obtain the IPN hydrogel.

The semi-IPN hydrogel is formed by dissolving a soluble polymer containing dye moieties in a mixture of monomers including a quencher monomer and through complex formation with the fluorophore. In some embodiments, the sensing moieties are immobilized by an insoluble polymer matrix which is freely permeable to polyhydroxyl compounds. Additional details on hydrogel systems have been disclosed in US Patent Publications Nos. US2004/0028612, and 2006/0083688 which are hereby incorporated by reference in their entireties.

The polymer matrix is comprised of organic, inorganic or combinations of polymers thereof. The matrix may be composed of biocompatible materials. Alternatively, the matrix is coated with a second biocompatible polymer that is permeable to the analytes of interest. The function of the polymer matrix is to hold together and immobilize the fluorescent dye and quencher moieties while at the same time allowing contact with the analytes (e.g., polyhydroxyl compounds, $H^+$ and $OH^-$), and binding of the polyhydroxyl compounds to the boronic acid. Therefore, the matrix is insoluble in the medium and in close association with it by establishing a high surface area interface between matrix and analyte solution. The matrix also does not interfere with transport of the analyte to the binding sites so that equilibrium can be established between the two phases. In one embodiment, an ultra-thin film or microporous support matrix may be used. In another embodiment, the matrix that is swellable in the analyte solution (e.g. a hydrogel matrix) can be used for aqueous systems. In some embodiments, the sensing polymers are bonded to a surface such as the surface of a light conduit, or impregnated in a microporous membrane. Techniques for preparing ultra-thin films, microporous polymers, microporous sol-gels, and hydrogels have been established in the prior art.

In one preferred embodiment, the boronic acid substituted viologen may be covalently bonded to a fluorescent dye. The adduct may be a polymerizable compound or a unit in a polymer. One such adduct for example may be prepared by first forming an unsymmetrical viologen from 4,4'-dipyridyl by attaching a benzyl-3-boronic acid group to one nitrogen and an aminoethyl group to the other nitrogen atom. The viologen is condensed sequentially first with 8-acetoxypyrene-1,3,6-trisulfonyl chloride in a 1:1 mole ratio followed by reaction with excess PEG diamine to obtain a prepolymer mixture. An acid acceptor is included in both steps to scavenge the byproduct acid. The prepolymer mixture is crosslinked by reaction with a polyisocyanate to obtain a hydrogel. The product is treated with base to remove the acetoxy blocking group. Incomplete reaction products and unreacted starting materials are leached out of the hydrogel by exhaustive extraction with deionized water before further use. The product is responsive to glucose when used as the sensing component as described herein.

Alternatively, such adducts are ethylenically unsaturated monomer derivatives. For example, dimethyl bis-bromomethyl benzene boronate is reacted with excess 4,4'-dipyridyl to form a half viologen adduct. After removing the excess dipyridyl, the adduct is further reacted with an excess of bromoethylamine hydrochloride to form the bis-viologen adduct. This adduct is coupled to a pyranine dye by reaction with the 8-acetoxypyrene-tris sulfonyl chloride in a 1:1 mole ratio in the presence of an acid acceptor followed by reaction with excess aminopropylmethacrylamide. Finally, any residual amino groups may be reacted with methacrylol chloride. After purification, the dye/viologen monomer may be copolymerized with HEMA and PEGDMA to obtain a hydrogel.

SOLUTION EXAMPLE

Figure 15:
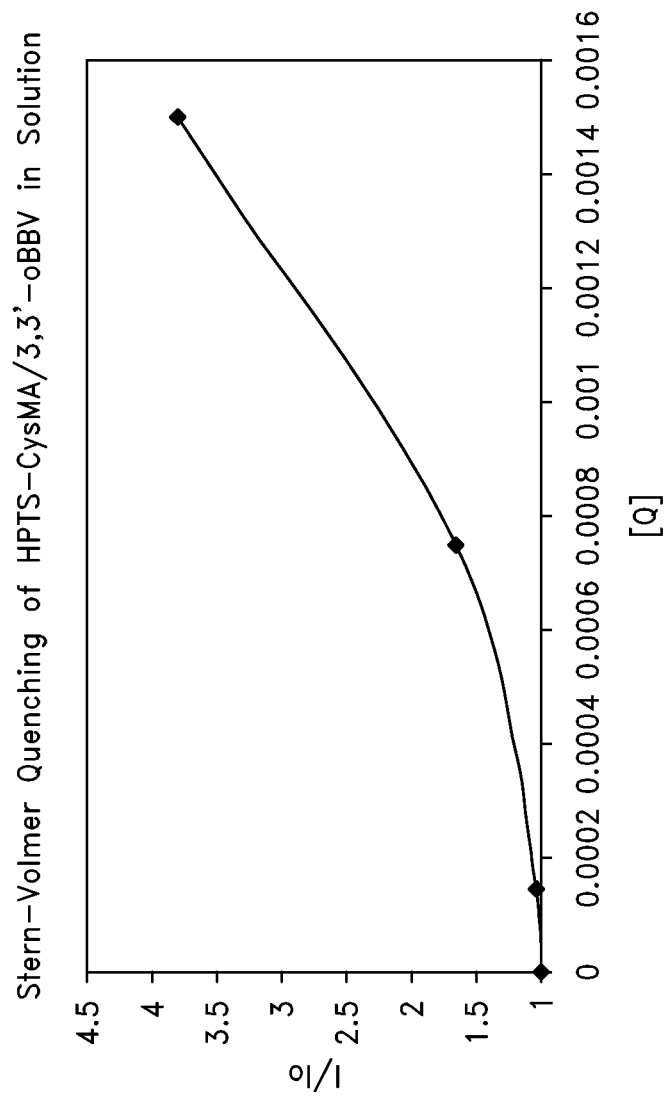
FIG. 15 shows the Stern-Volmer quenching of HPTS-CysMA/3,3'-oBBV in solution.

To a solution of HPTS-CysMA ($1 \times 10^{-5}$ M in pH 7.4 PBS) was added increasing amounts of 3,3'-oBBV (30 mM in MeOH) and the fluorescence emission measured after each addition. FIG. 15 gives the relative emission change (Stern-Volmer curve) upon addition of 3,3'-oBBV (Q) indicating the quenching of HPTS-CysMA with 3,3'-oBBV. The fluorimeter settings were as follows: 1% attenuation, ex slit 8 nm, em slit 12 nm, 486 nm ex $\lambda$, 537 nm em $\lambda$.

Figure 16:
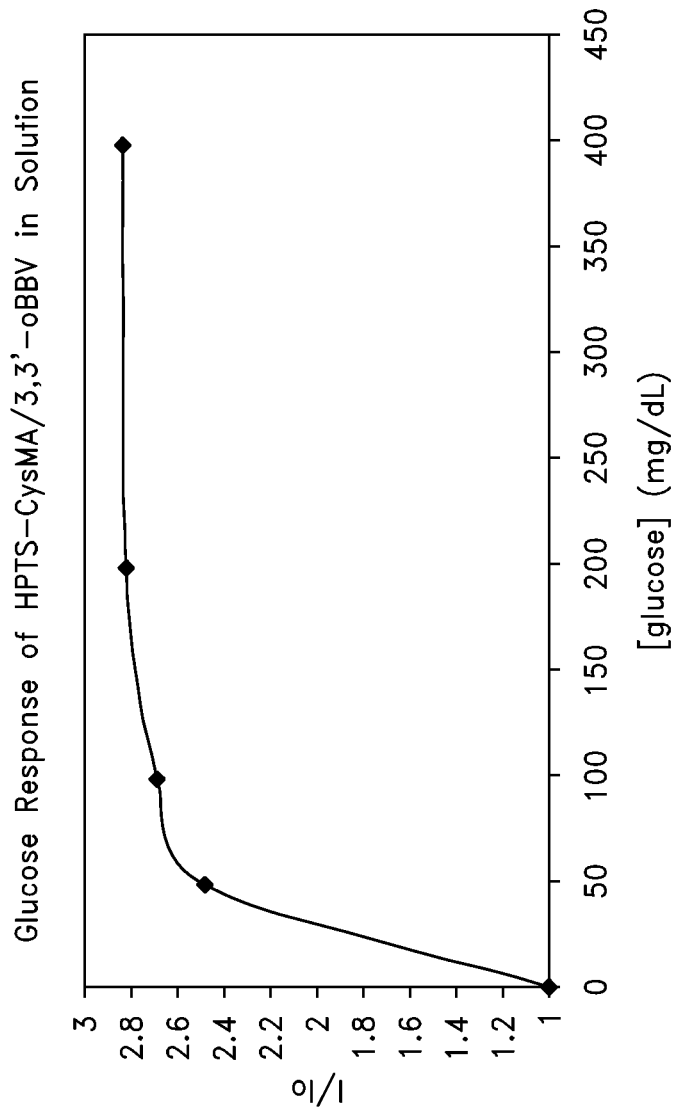
FIG. 16 shows the glucose response of HPTS-CysMA/3,3'-oBBV in solution.

HPTS-CysMA ($1 \times 10^{-5}$ M) and 3,3'-oBBV ($3 \times 10^{-3}$ M) were titrated with a stock solution of glucose (31250 mg/dL) in pH 7.4 PBS and the fluorescence emission measured after each addition of glucose. The relative change upon addition of glucose is given in FIG. 16.

HYDROGEL EXAMPLE

Figure 17:
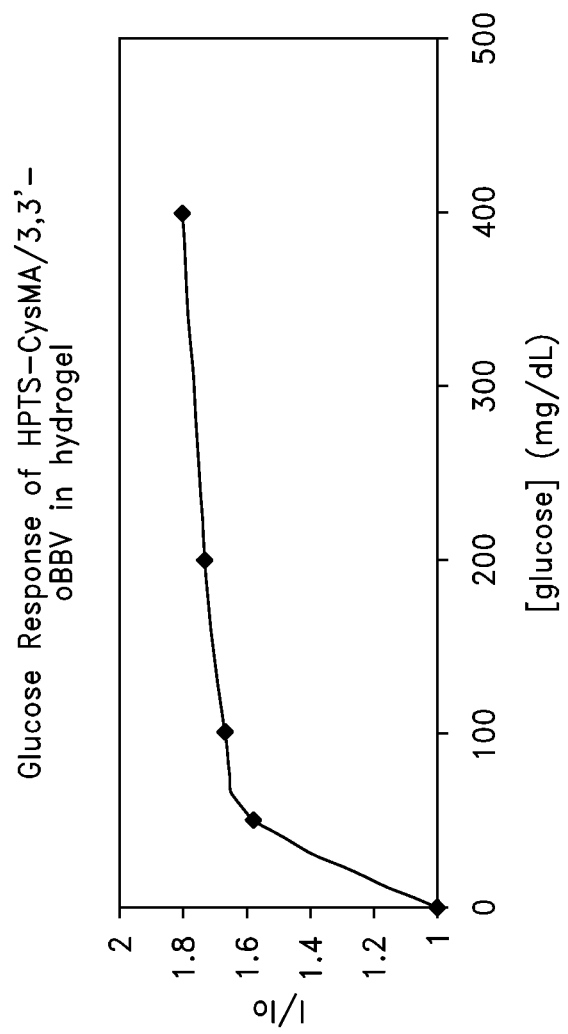
FIG. 17 shows the glucose response of HPTS-CysMA/3,3'-oBBV in hydrogel.

HPTS-CysMA (2 mg), 3,3'-oBBV (15 mg), N,N'-dimethylacrylamide (400 mg), N,N'-methylenebisacrylamide (8 mg), HCl (10 μL of 1 M solution), and VA-044 (1 mg) were dissolved in water and diluted to 1 mL in a volumetric flask. The solution was freeze-pump-thawed (3×), injected into a mold containing a 0.005" polyimide spacer and polymerized at 55° C. for 16 h. The resultant film was placed in pH 7.4 phosphate buffer and was tested in a flow cell configuration with increasing amounts of glucose (0, 50, 100, 200, 400 mg/dL). The relative fluorescence change upon addition of glucose is given in FIG. 17. The fluorimeter settings were as follows: ex slit 8 nm, em slit 3.5 nm, 515 nm cutoff filter, 486 nm ex $\lambda$, 532 nm em $\lambda$.

Although the foregoing invention has been described in terms of certain embodiments and examples, other embodiments will be apparent to those of ordinary skill in the art from the disclosure herein. Moreover, the described embodiments have been presented by way of example only, and are not intended to limit the scope of the inventions. Indeed, the novel methods and systems described herein may be embodied in a variety of other forms without departing from the spirit thereof. Accordingly, other combinations, omissions, substitutions and modifications will be apparent to the skilled artisan in view of the disclosure herein. Thus, the present invention is not intended to be limited by the example or preferred embodiments. The accompanying claims provide exemplary claims and their equivalents are intended to cover forms or modifications as would fall within the scope and spirit of the inventions.

What is claimed is:

1. A sensor for detecting an analyte concentration in a blood vessel, comprising:
    an optical fiber with proximal and distal ends;
    an atraumatic tip portion with proximal and distal ends, wherein the proximal end of the atraumatic tip portion is separated from the distal end of the optical fiber, such that a gap exists between the atraumatic tip portion and the optical fiber;
    a rod with proximal and distal ends, wherein the proximal end of the rod is attached to the distal end of the optical fiber, and wherein the distal end of the rod is attached to the proximal end of the atraumatic tip portion, such that the rod traverses the gap and couples the optical fiber to the atraumatic tip portion;
    a chemical indicator system disposed within the gap and capable of generating an emission light signal in response to an excitation light signal, wherein the intensity of the emission light signal is related to the analyte concentration; and
    a selectively permeable membrane disposed over the gap, wherein the sensor is sized for deployment within the blood vessel.

2. The sensor of claim 1, wherein the chemical indicator system is further immobilized within the gap by a hydrogel.

3. The sensor of claim 1, further comprising a temperature sensor.

4. The sensor of claim 1, wherein the optical fiber has a diameter of between about 0.005 inches and about 0.020 inches.

5. The sensor of claim 1, further comprising a reflective region.

6. The sensor of claim 5, wherein the reflective region comprises a reflective surface of the proximal end of the rod.

7. The sensor of claim 1, wherein the rod is attached to the optical fiber by heating.

8. The sensor of claim 1, wherein the rod is attached to the optical fiber by a reflective adhesive.

9. The sensor of claim 8, wherein the shape of the distal end of the atraumatic tip portion is configured to reduce trauma within the blood vessel and selected from the group consisting of hemispherical, parabolic, and elliptical.

10. The sensor of claim 1, wherein the distal end of the atraumatic tip portion is flexible.

11. The sensor of claim 1, wherein the distal end of the atraumatic tip portion is deformable.

12. The sensor of claim 1, wherein the distal end of the atraumatic tip portion is formed from at least one material selected from the group consisting of plastics, polymers, gels, metals and composites.

13. The sensor of claim 1, wherein the rod is formed from at least one material selected from the group consisting of metal, metal alloy, plastic, polymer, ceramic, and composite material.

14. The sensor of claim 13, wherein the rod is formed from stainless steel, titanium, or Nitinol.

15. The sensor of claim 1, wherein the rod is cylindrical.

16. The sensor of claim 15, wherein the rod diameter is between about 0.002 inches and about 0.010 inches.

17. The sensor of claim 1, wherein the rod is flexible.

18. The sensor of claim 1, wherein the rod is stiffer than the optical fiber.

19. The sensor of claim 1, wherein the rod is sufficiently stiff to prevent flexing of the sensor along the gap.

20. A sensor for detecting an analyte concentration in a blood vessel, comprising:
   an optical fiber with proximal and distal ends;
   an atraumatic tip portion with proximal and distal ends, wherein the proximal end of the atraumatic tip portion is separated from the distal end of the optical fiber, such that a gap exists between the atraumatic tip portion and the optical fiber;
   a hypotube with proximal and distal ends, wherein the proximal end of the hypotube is attached to the distal end of the optical fiber, and wherein the distal end of the hypotube is attached to the proximal end of the atraumatic tip portion, such that the hypotube traverses the gap and couples the optical fiber to the atraumatic tip portion, wherein the hypotube comprises at least one window that opens onto the gap;
   a chemical indicator system disposed within the gap and capable of generating an emission light signal in response to an excitation light signal, wherein the intensity of the emission light signal is related to the analyte concentration; and
   a selectively permeable membrane disposed over the at least one window, wherein the sensor is sized for deployment within the blood vessel.

21. The sensor of claim 20, wherein the chemical indicator system is further immobilized within the gap by a hydrogel.

22. A sensor for detecting an analyte concentration in a blood vessel, comprising:
   an optical fiber with proximal and distal ends;
   an atraumatic tip portion with proximal and distal ends, wherein the proximal end of the atraumatic tip portion is separated from the distal end of the optical fiber, such that a gap exists between the atraumatic tip portion and the optical fiber;
   a cage connecting the optical fiber and atraumatic tip portion, wherein the optical fiber is at least partially enclosed within the cage, and wherein the cage has at least one window;
   a chemical indicator system disposed within the cage, wherein the chemical indicator system is adjacent the window and is separated from analyte by a selectively permeable membrane, and wherein the chemical indicator system is capable of generating an emission light signal in response to an excitation light signal, wherein the intensity of the emission light signal is related to the analyte concentration; and
   a reference material, wherein the reference material is configured to either reflect a portion of the excitation light signal before the excitation light signal enters the chemical indicator system or to return a second emission light signal, wherein the intensity of the second emission light signal is not related to the analyte concentration.

23. A sensor for detecting an analyte concentration in a blood vessel, comprising:
   an optical fiber with a proximal end and a distal end, wherein the distal end of the optical fiber comprises a glucose sensing hydrogel and wherein the glucose sensing hydrogel comprises a first fluorophore, a quencher, and at least one glucose binding moiety;
   a reference fiber adjacent the optical fiber having a proximal end and a distal end, wherein the distal end of the reference fiber comprises a reference material, wherein the reference material comprises a second fluorophore;
   a light emitting diode operably coupled to the glucose fiber and the reference fiber, wherein the light emitting diode sends an excitation light to the glucose fiber and the reference fiber;
   a glucose signal detector operatively coupled to the glucose fiber, wherein the glucose signal detector receives a first fluorescent light from the glucose fiber; and
   a reference signal detector operatively coupled to the reference fiber, wherein the reference signal detector receives a second fluorescent light from the reference fiber.

24. The sensor of claim 23, wherein the first fluorophore is the same as the second fluorophore.

25. The sensor of claim 23, wherein the first fluorophore is different than the second fluorophore.

26. The sensor of claim 23, wherein the reference material comprises a quencher.

27. The sensor of claim 23, wherein the reference material is encased in a glucose impermeable membrane.

* * * * *

UNITED STATES PATENT AND TRADEMARK OFFICE
CERTIFICATE OF CORRECTION

| | |
|---|---|
| PATENT NO. | : 8,467,843 B2 |
| APPLICATION NO. | : 12/612602 |
| DATED | : June 18, 2013 |
| INVENTOR(S) | : Markle et al. |

It is certified that error appears in the above-identified patent and that said Letters Patent is hereby corrected as shown below:

Title Page

In column 1 (page 4 item 56) at line 60, Under Other Publications, change "6-methylquoliniurn" to --6-methylquinolinium--.

In column 2 (page 4 item 56) at line 38, Under Other Publications, change "Suprarnolecular" to --Supramolecular--.

In the Specification

In column 5 at line 36, Change "minor," to --mirror,--.

In column 9 at line 36, Change "minor)" to --mirror)--.

In column 11 at line 56, Change "minor" to --mirror--.

In column 12 at line 15, Change "minor)" to --mirror)--.

In column 13 at line 20, Change "minor" to --mirror--.

In column 14 at line 20, Change "minor" to --mirror--.

Signed and Sealed this
Nineteenth Day of November, 2013

Teresa Stanek Rea
*Deputy Director of the United States Patent and Trademark Office*